(12) United States Patent
Avidano et al.

(10) Patent No.: US 12,329,417 B2
(45) Date of Patent: Jun. 17, 2025

(54) MODULAR TENSIONED SPINAL SCREW

(71) Applicant: SPINE WAVE, INC., Shelton, CT (US)

(72) Inventors: Eugene Avidano, Stratford, CT (US);
Peter Barreiro, Trumbull, CT (US);
Daniel Vigliotti, Guilford, CT (US)

(73) Assignee: SPINE WAVE, INC., Shelton, CT (US)

( * ) Notice: Subject to any disclaimer, the term of this patent is extended or adjusted under 35 U.S.C. 154(b) by 661 days.

(21) Appl. No.: 17/544,523

(22) Filed: Dec. 7, 2021

(65) Prior Publication Data
US 2022/0133363 A1     May 5, 2022

Related U.S. Application Data

(63) Continuation of application No. 16/843,160, filed on Apr. 8, 2020, now Pat. No. 11,219,470.
(Continued)

(51) Int. Cl.
*A61B 17/70*     (2006.01)
*A61B 17/86*     (2006.01)

(52) U.S. Cl.
CPC ...... *A61B 17/7032* (2013.01); *A61B 17/7052* (2013.01); *A61B 17/8605* (2013.01)

(58) Field of Classification Search
CPC ............ A61B 17/7032; A61B 17/7035; A61B 17/7037
See application file for complete search history.

(56) References Cited

U.S. PATENT DOCUMENTS

| | | |
|---|---|---|
| 6,837,889 B2 | 1/2005 | Shluzas |
| 7,066,937 B2 | 6/2006 | Shluzas |
| | (Continued) | |

FOREIGN PATENT DOCUMENTS

| | | |
|---|---|---|
| JP | 2008523890 | 7/2008 |
| JP | 2015131110 | 7/2015 |
| | (Continued) | |

OTHER PUBLICATIONS

International Search Report for PCT/US2021/013253, mailed Jul. 5, 2021.
(Continued)

*Primary Examiner* — Eduardo C Robert
*Assistant Examiner* — Michelle C Green
(74) *Attorney, Agent, or Firm* — Hoffmann & Baron, LLP

(57) ABSTRACT

A modular tensioned spinal screw comprises a bone fastener having a threaded elongate shaft and a spherical head at an upper end of said shaft. A modular yoke for polyaxial attachment to the head of said bone fastener has an inner bore, an upper end configured to receive a connecting rod and a lower end configured to receive the head of the bone fastener. An axially movable radially expandable socket collar, and a saddle having a rod receiving cradle are supported within the yoke bore. A retention pin fixed to the yoke movably supports the saddle and a tension member within the bore. The tension member comprises a resilient biasing element oriented such that upward axial movement of the saddle produces a downward bias force on said saddle to compress the head of the bone fastener between said saddle and said socket collar in a provisional holding position.

18 Claims, 20 Drawing Sheets

Related U.S. Application Data

(60) Provisional application No. 62/880,188, filed on Jul. 30, 2019.

(56) References Cited

U.S. PATENT DOCUMENTS

| | | | |
|---|---|---|---|
| 7,087,057 | B2 | 8/2006 | Konieczynski |
| 7,678,139 | B2 | 3/2010 | Garamszegi |
| 7,875,065 | B2 | 1/2011 | Jackson |
| 7,879,075 | B2 | 2/2011 | Shluzas |
| 7,947,065 | B2 | 5/2011 | Hammill |
| 8,197,518 | B2 | 6/2012 | Hammill |
| 8,366,747 | B2 | 2/2013 | Shluzas |
| 8,709,050 | B2 | 4/2014 | Shluzas |
| 8,926,671 | B2 | 1/2015 | Biedermann |
| 8,936,624 | B2 | 1/2015 | Shluzas |
| 8,951,290 | B2 | 2/2015 | Hammer |
| 9,498,255 | B2 | 11/2016 | Lovell |
| 9,848,913 | B2 | 12/2017 | Shluzas |
| 9,943,338 | B2 | 4/2018 | Biedermann et al. |
| 10,076,361 | B2 | 9/2018 | Jackson |
| 10,194,951 | B2 | 2/2019 | Jackson |
| 10,219,835 | B2 | 3/2019 | Shluzas |
| 10,278,738 | B2 | 5/2019 | Jackson |
| 10,448,976 | B2 | 10/2019 | Matthis |
| 10,485,594 | B2 | 11/2019 | Toon |
| 10,561,453 | B2 | 2/2020 | Rezach |
| 2006/0149233 | A1 | 7/2006 | Richelsoph |
| 2007/0118123 | A1 | 5/2007 | Strausbaugh et al. |
| 2008/0243193 | A1* | 10/2008 | Ensign ............... A61B 17/7037 606/301 |
| 2011/0009911 | A1* | 1/2011 | Hammill, Sr. ..... A61B 17/7038 606/308 |
| 2015/0032162 | A1* | 1/2015 | Biedermann ...... A61B 17/7035 606/278 |
| 2015/0196337 | A1 | 7/2015 | Biedermann et al. |
| 2015/0196338 | A1 | 7/2015 | Biedermann et al. |
| 2016/0262816 | A1 | 9/2016 | Doubler et al. |
| 2017/0027614 | A1 | 2/2017 | Biedermann et al. |
| 2017/0172630 | A1* | 6/2017 | Biedermann ...... A61B 17/7002 |
| 2019/0223917 | A1 | 7/2019 | Gray |
| 2020/0375638 | A1 | 12/2020 | Avidano et al. |
| 2021/0030445 | A1 | 2/2021 | Avidano et al. |

FOREIGN PATENT DOCUMENTS

| | | |
|---|---|---|
| JP | 2015131111 | 7/2015 |
| WO | 2006065342 A2 | 6/2006 |
| WO | 2006/116437 | 11/2006 |

OTHER PUBLICATIONS

Written Opinion of the International Searching Authority for PCT/US2021/013253, mailed Jul. 5, 2021.

* cited by examiner

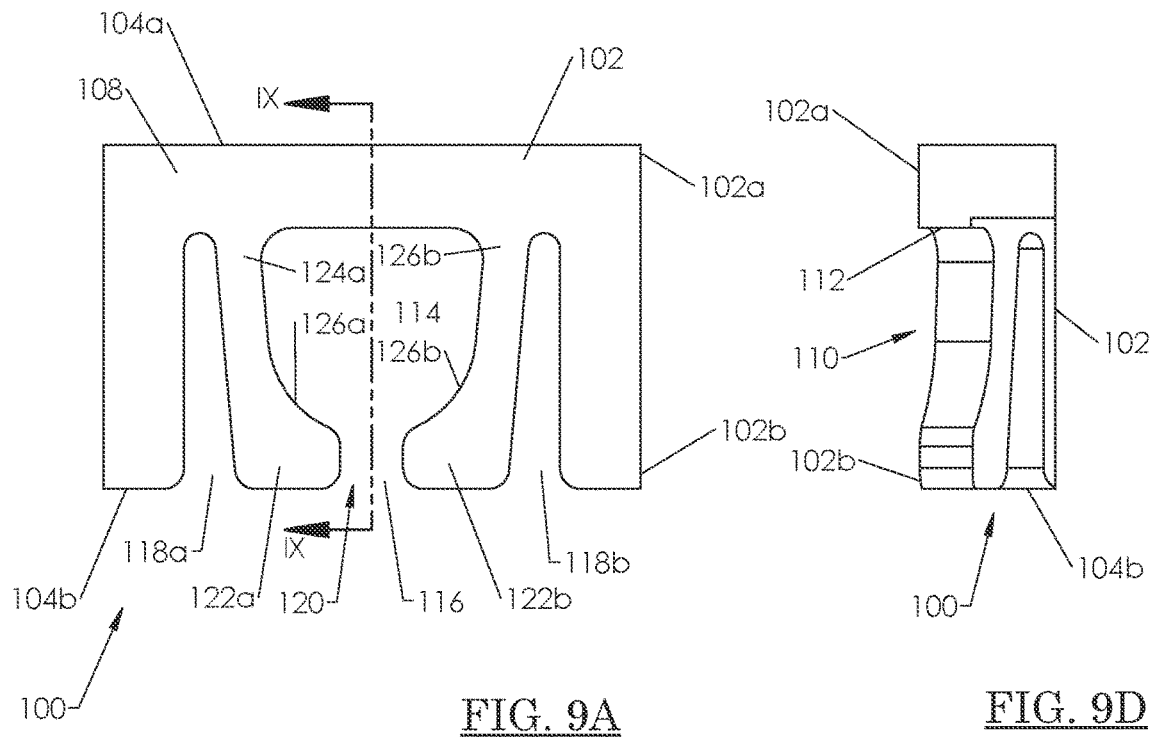
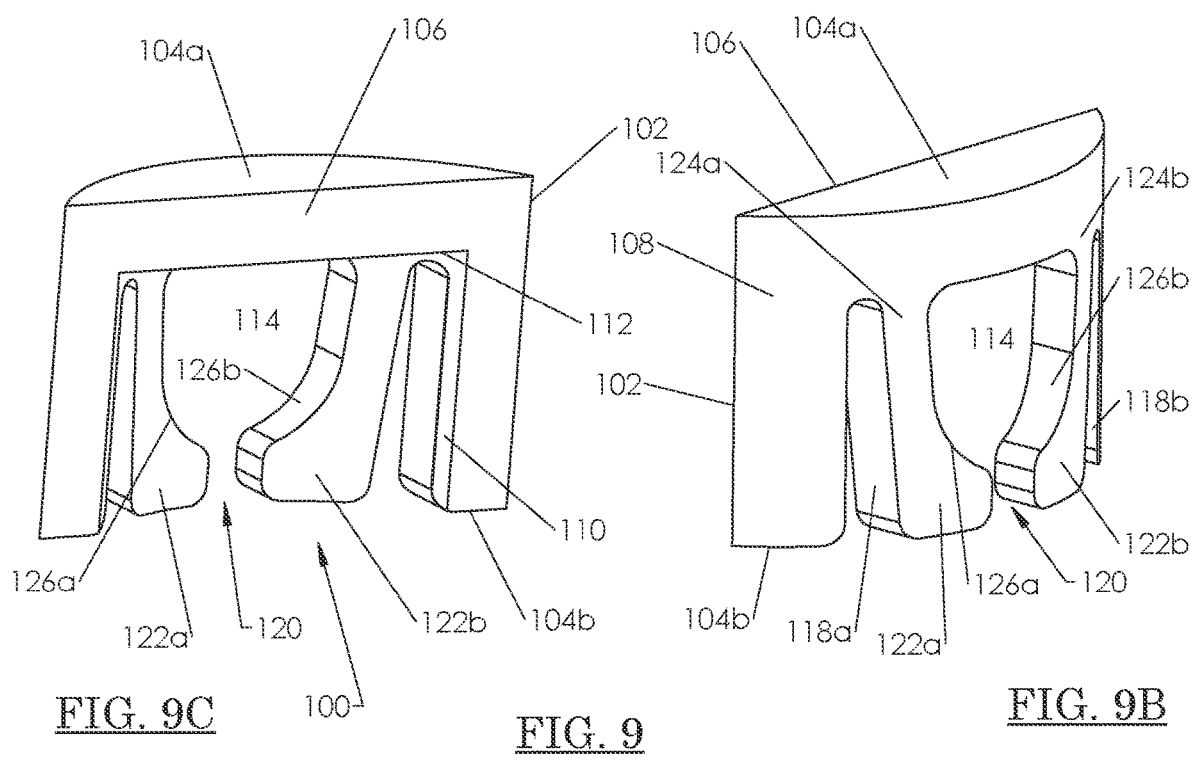
FIG. 9A  FIG. 9D  FIG. 9C  FIG. 9B  FIG. 9

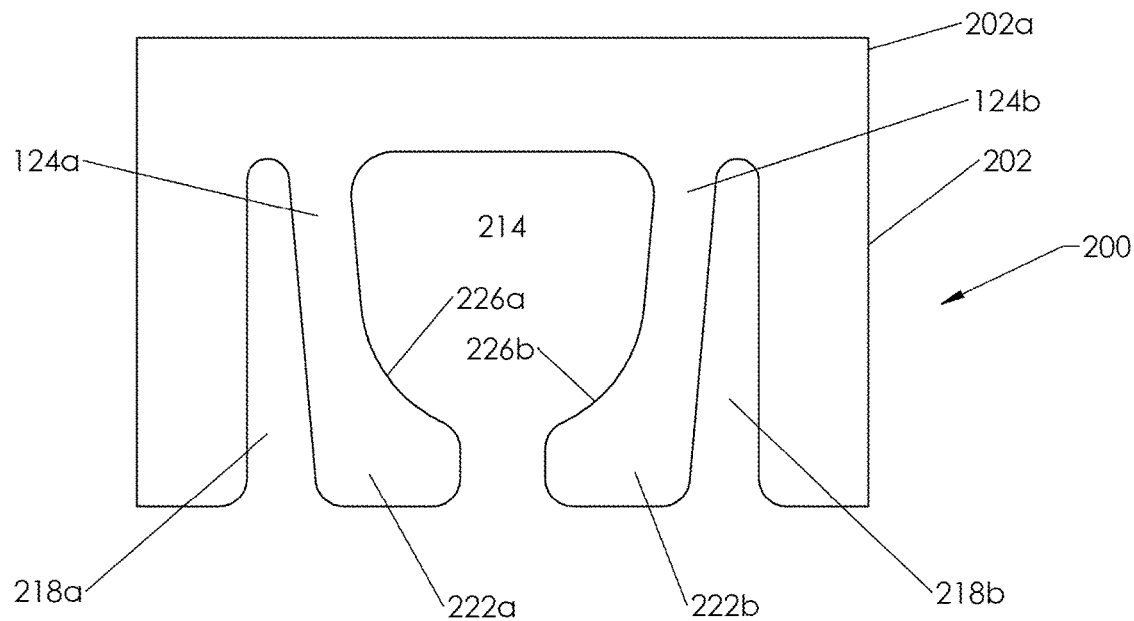
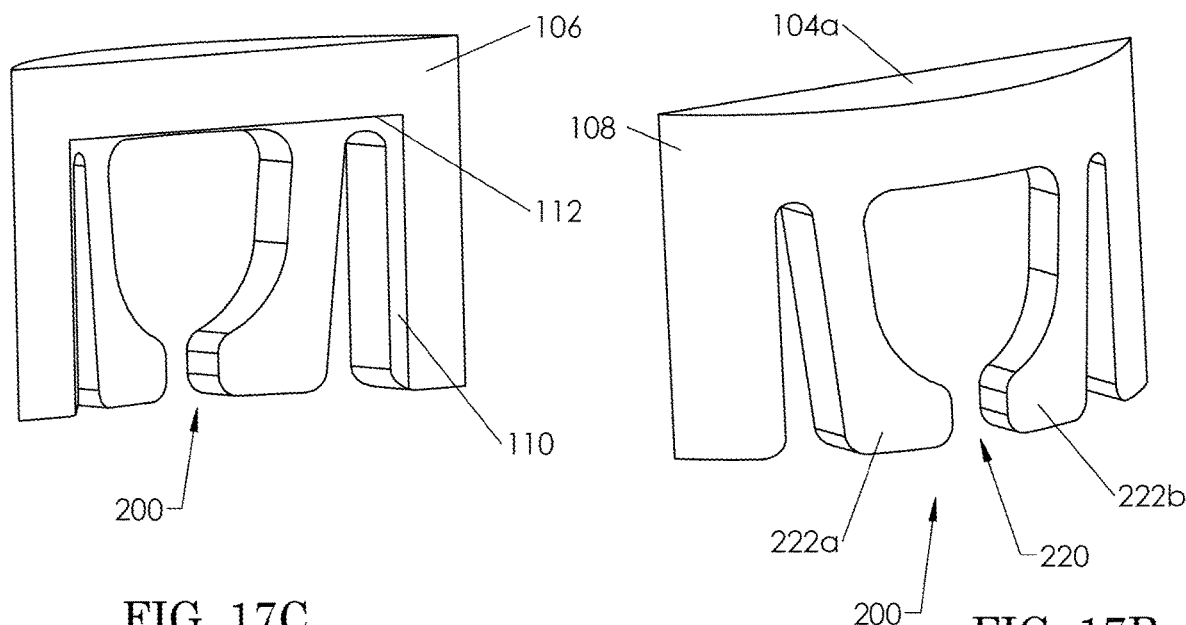
FIG. 17C
FIG. 17B
FIG. 17

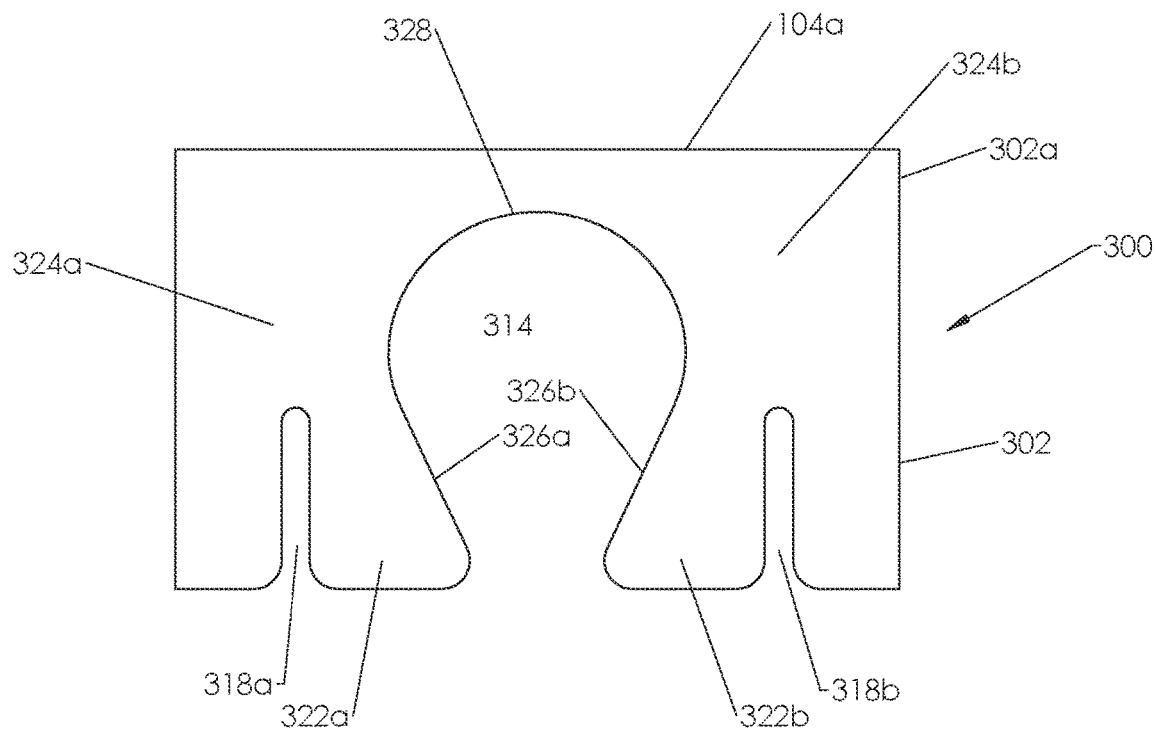
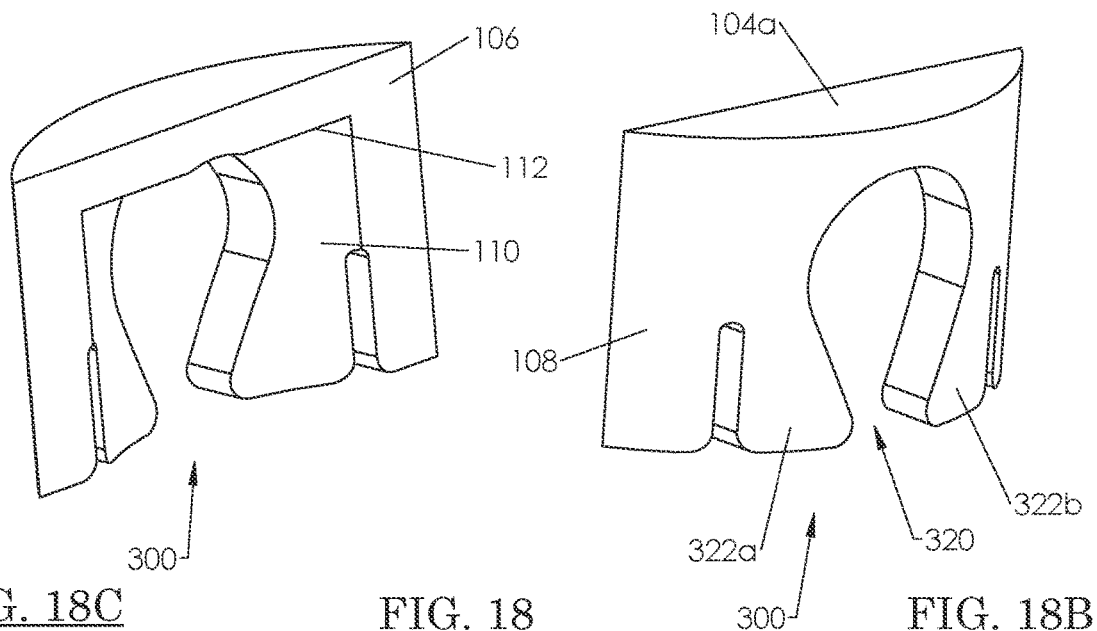
FIG. 18C    FIG. 18    FIG. 18B

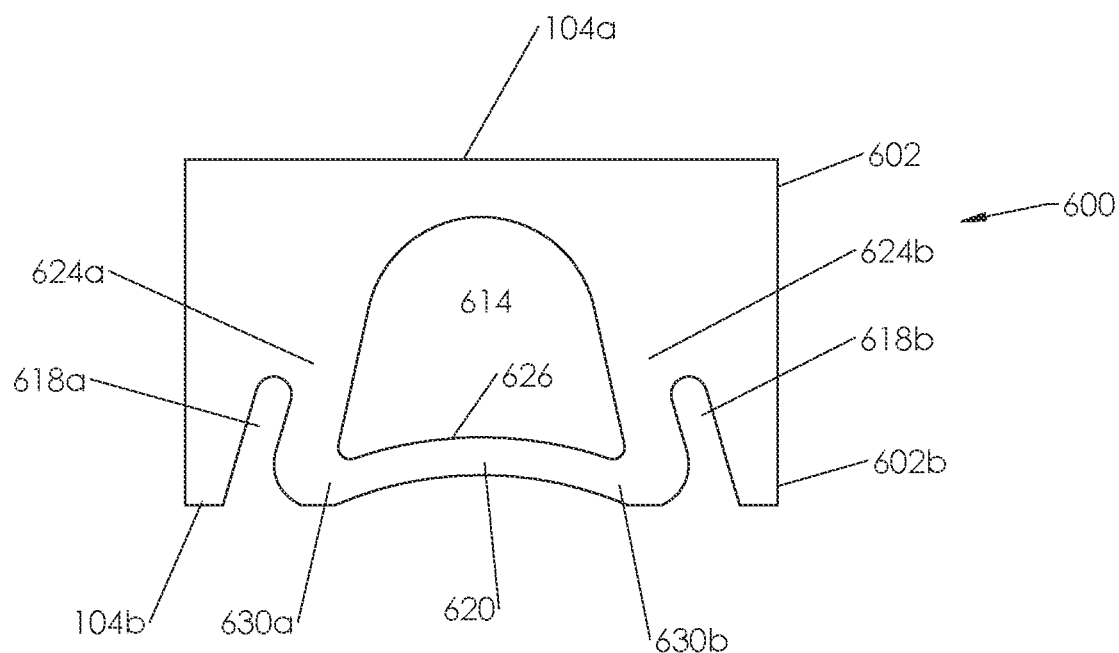
FIG. 21A
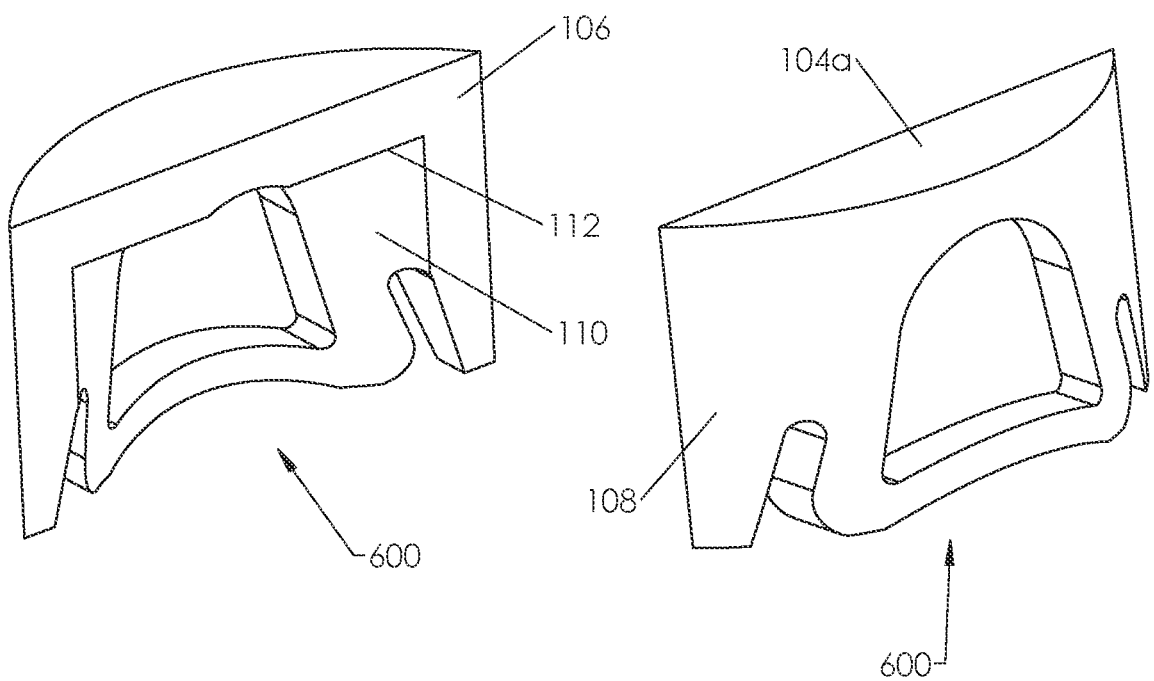
FIG. 21C
FIG. 21B
FIG. 21

MODULAR TENSIONED SPINAL SCREW

CROSS-REFERENCE TO RELATED APPLICATION

This application is a continuation application of U.S. application Ser. No. 16/843,160, filed Apr. 8, 2020, now allowed, which claims the benefit of U.S. Provisional Patent Application No. 62/880,188, filed Jul. 30, 2019, the entire contents of which are incorporated by reference herein.

FIELD OF THE INVENTION

The subject invention relates to a spinal screw, and more particularly to a modular spinal screw that includes a yoke that is polyaxially attachable to a threaded bone fastener and tensioned in a manner to frictionally hold the yoke and bone fastener in a provisional position prior to locking with a spinal connecting rod.

BACKGROUND OF THE INVENTION

Traditional polyaxial pedicle screws comprise an elongate shaft threaded at one end and a head, typically having a spherical surface, at the other end. A yoke having a U-shaped opening for receiving a spinal fixation rod is typically pre-assembled to the screw head in a manner to allow articulating movement of the yoke relative to the threaded shaft. It is known that in certain traditional polyaxial pedicle screws a structure is configured to provide sufficient friction between the spherical head of the bone screw and the yoke to enable the bone screw shank to be maintained in a desired angular orientation before locking the spherical head within the yoke. Such an arrangement is shown, for example, in U.S. Pat. No. 7,087,057, entitled "Polyaxial Bone Screw", issued on Aug. 8, 2006 to Konieczynski et al.

In a modular pedicle screw construction, the yoke is configured to be articulatingly attached to the screw head in situ subsequent to the threaded installation of the threaded shaft into a pedicle. An inserter may be used to hold and properly attach the yoke to a head of a bone screw in situ after threaded installation of the bone screw into a pedicle of a vertebra of a spine. Certain efforts have been made to provide modular tensioned pedicle screws wherein the modular yoke may be attached to the spherical head of the pedicle screw with sufficient friction for provisional holding. One example of such structure is shown and described in U.S. Pat. No. 9,498,255, entitled "Translational Pedicle Screw Systems", issued on Nov. 22, 2016 to Lovell et al. Lovell et al. describe a yoke, or saddle, that includes biasing components that are provided to increase frictional forces that bias against the saddle and the removable bone screw head.

Nevertheless, there is a desire for a modular tensioned polyaxial screw that provides effective provisional friction for holding the module yoke in a provisional position prior to locking with a spinal connecting rod.

SUMMARY OF THE INVENTION

It is an object of the invention to provide a modular tensioned spinal screw. It is a further object of the invention to provide a modular yoke assembly for polyaxial tensioned attachment to a head of a bone screw in situ during spinal surgery. It is another object of the invention to provide a kit of parts for use in spinal surgery comprising a plurality of modular yoke assemblies and a plurality of bone screw

BRIEF DESCRIPTION OF THE DRAWING FIGURES

Figure 2:
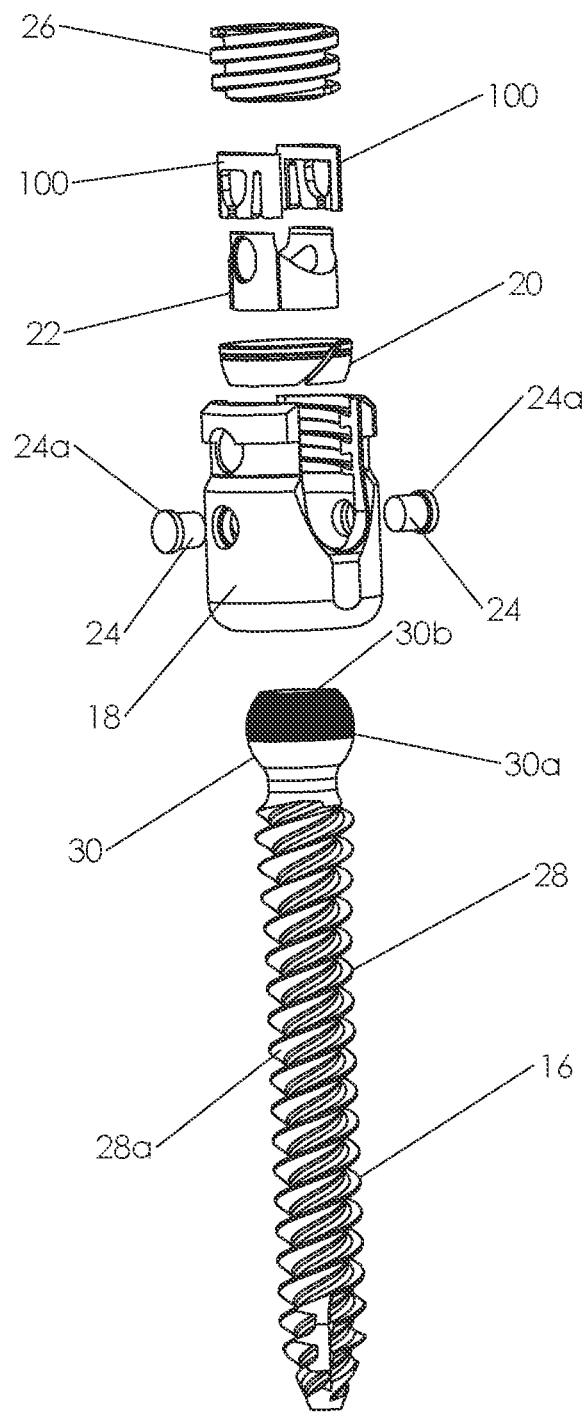
FIG. 2 is a top perspective exploded view of the modular tensioned polyaxial pedicle screw of FIG. 1 showing the constituent components thereof.

FIG. 9, which includes FIGS. 9A through 9D illustrates a first embodiment of one of the tension members of the modular tensioned polyaxial pedicle screw of FIG. 2, with FIG. 9A showing a side elevation view of the tension member, FIG. 9B showing a front perspective view of the tension member, FIG. 9C showing a rear perspective view of the tension member, and FIG. 9D showing a cross-section of the tension member as seen along viewing lines IX-IX of FIG. 9A.

Figure 10:
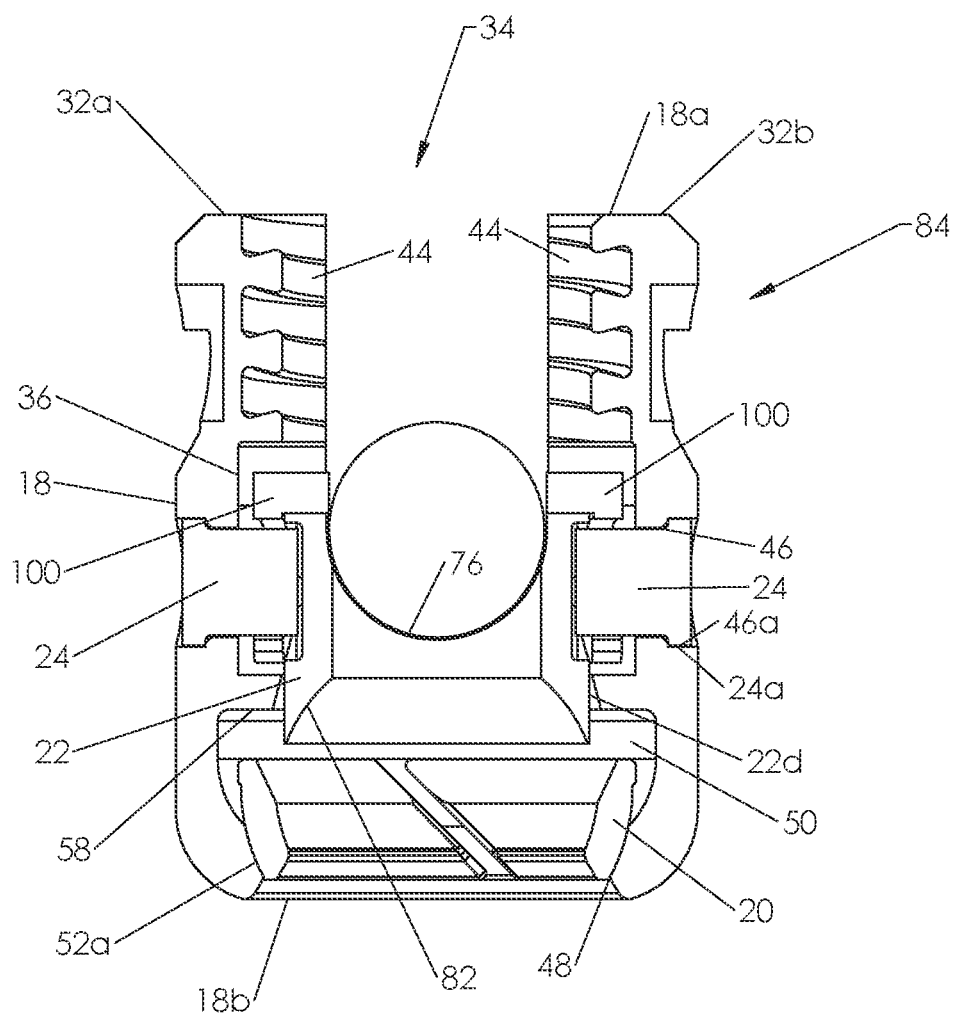

FIG. 10 is a cross-sectional view of the modular yoke assembly prior to modular connection to a pedicle screw.

Figure 11:
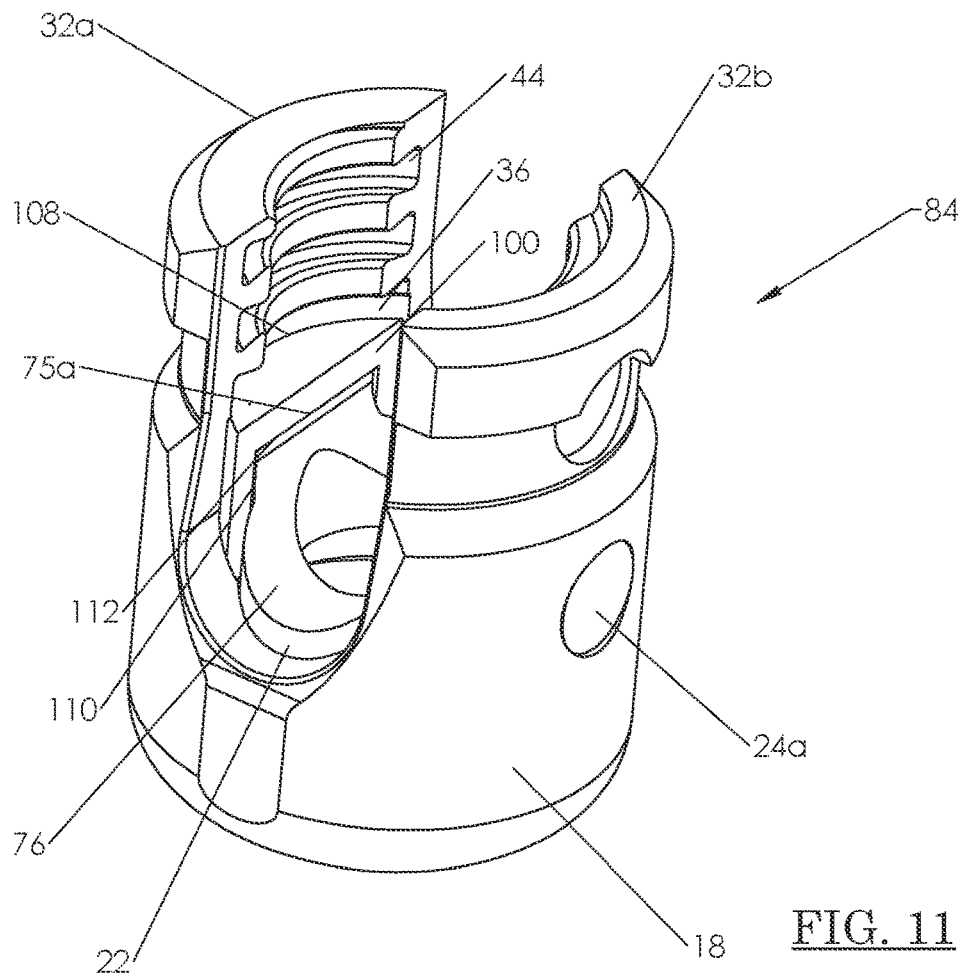

FIG. 11 is a top perspective view of the modular yoke assembly of FIG. 10.

Figure 12:
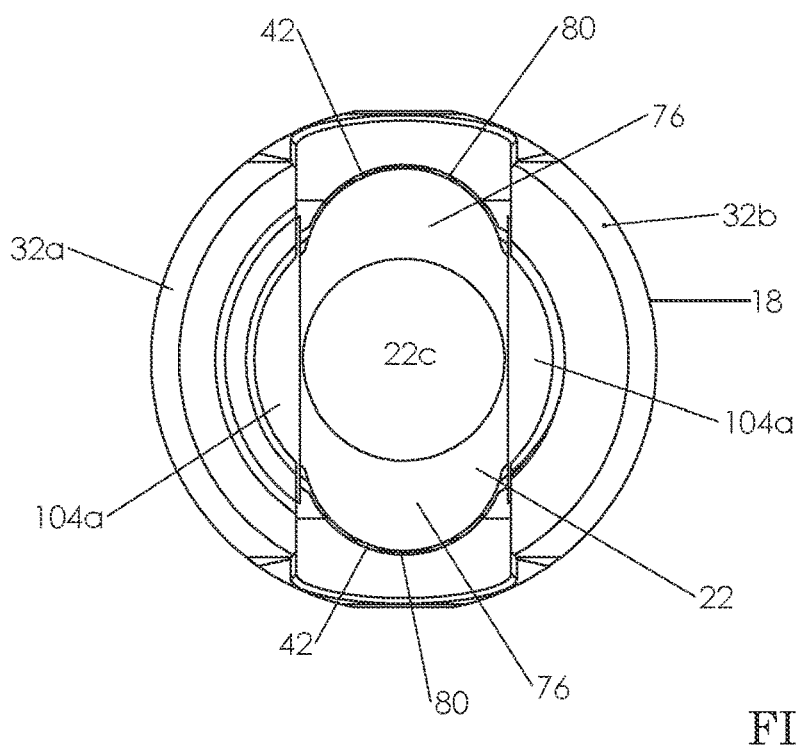

FIG. 12 is a top plan view of the modular yoke assembly of FIG. 10.

Figure 13:
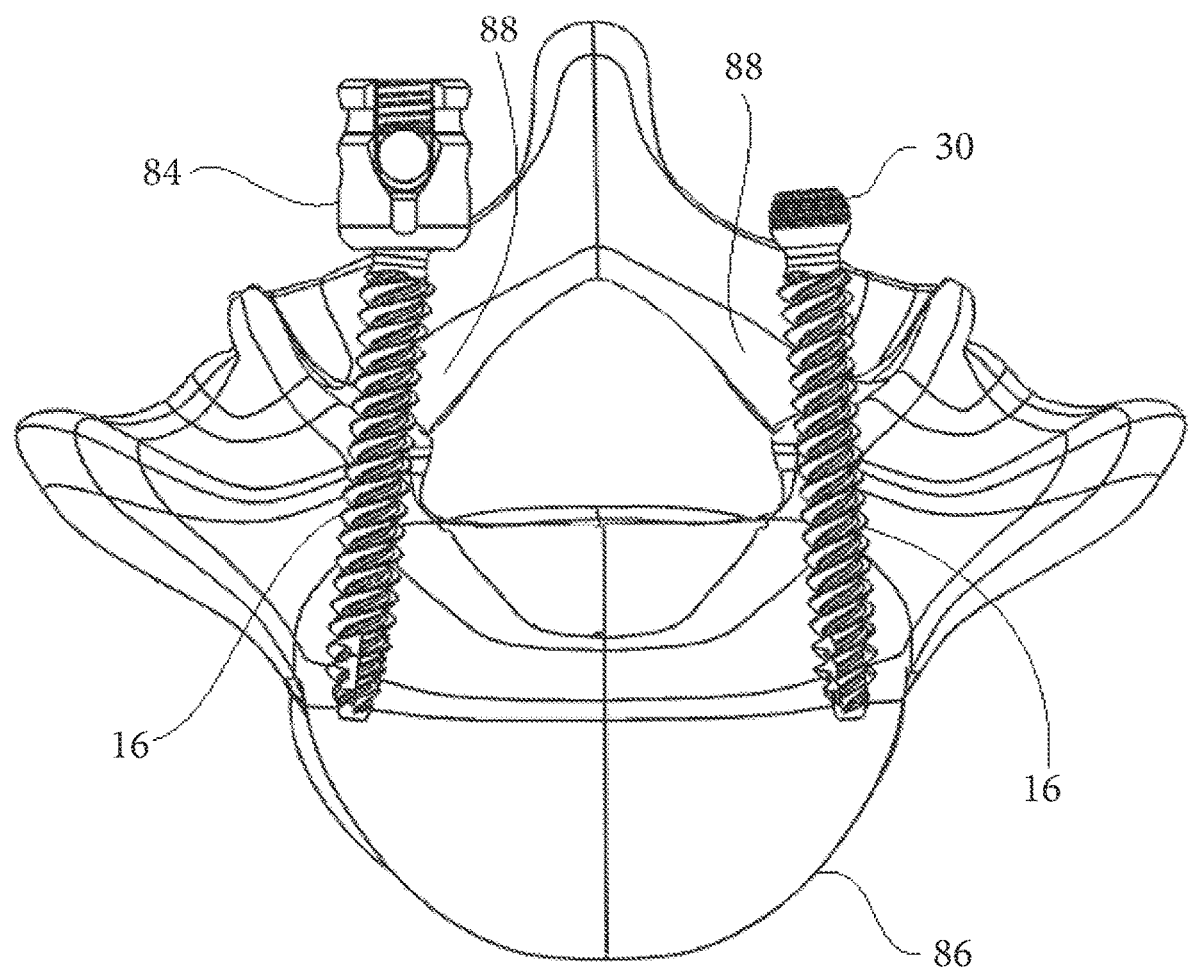

FIG. 13 is a cross-sectional view of a portion of a spine of a patient showing steps of attaching the modular polyaxial pedicle screw to a vertebra.

Figure 14A:
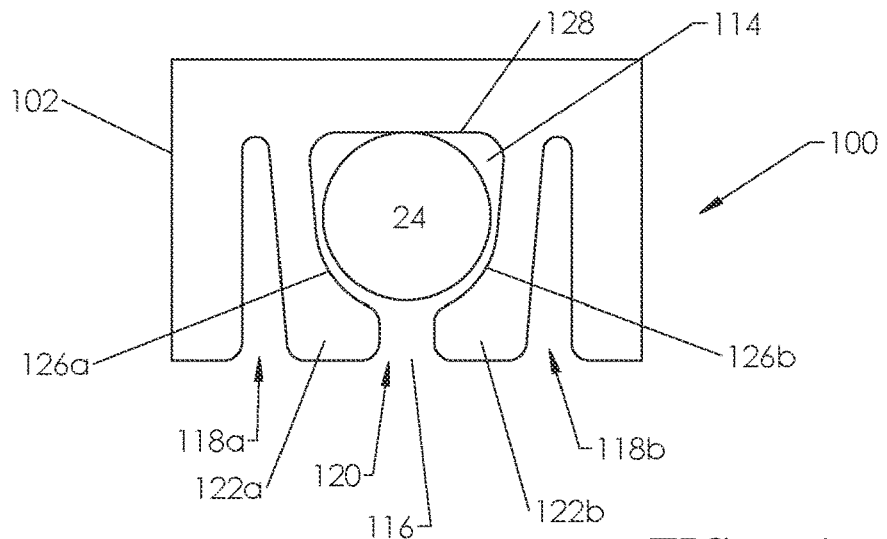
Figure 14B:
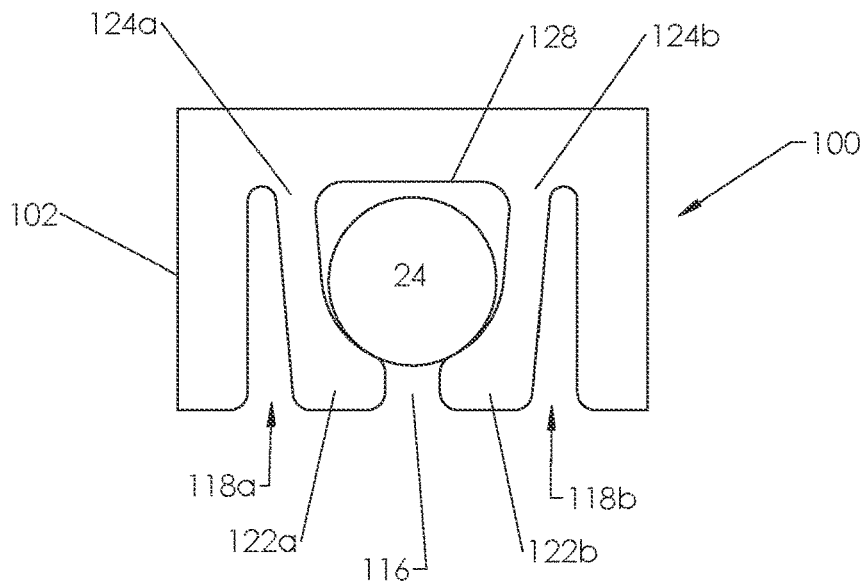
Figure 14C:
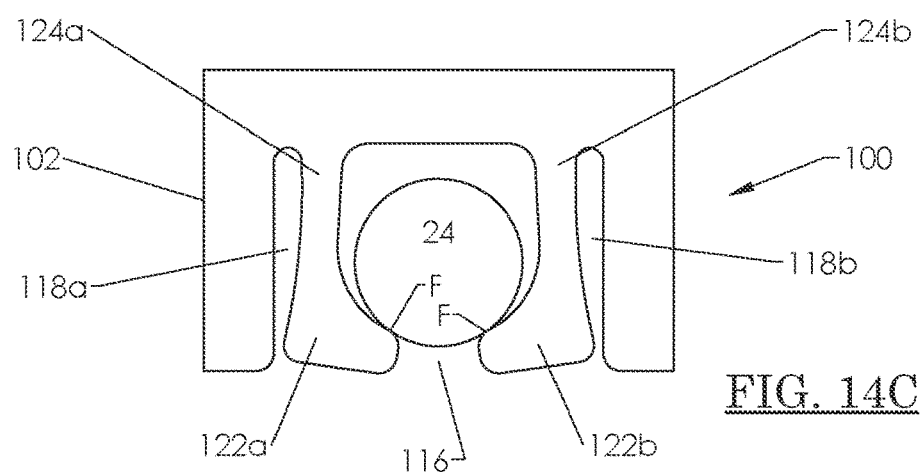

FIGS. 14A, 14B and 14C show stages of movement of the tension member of FIG. 9 in a manner to provide tension to the modular tensioned polyaxial pedicle screw.

Figure 15:
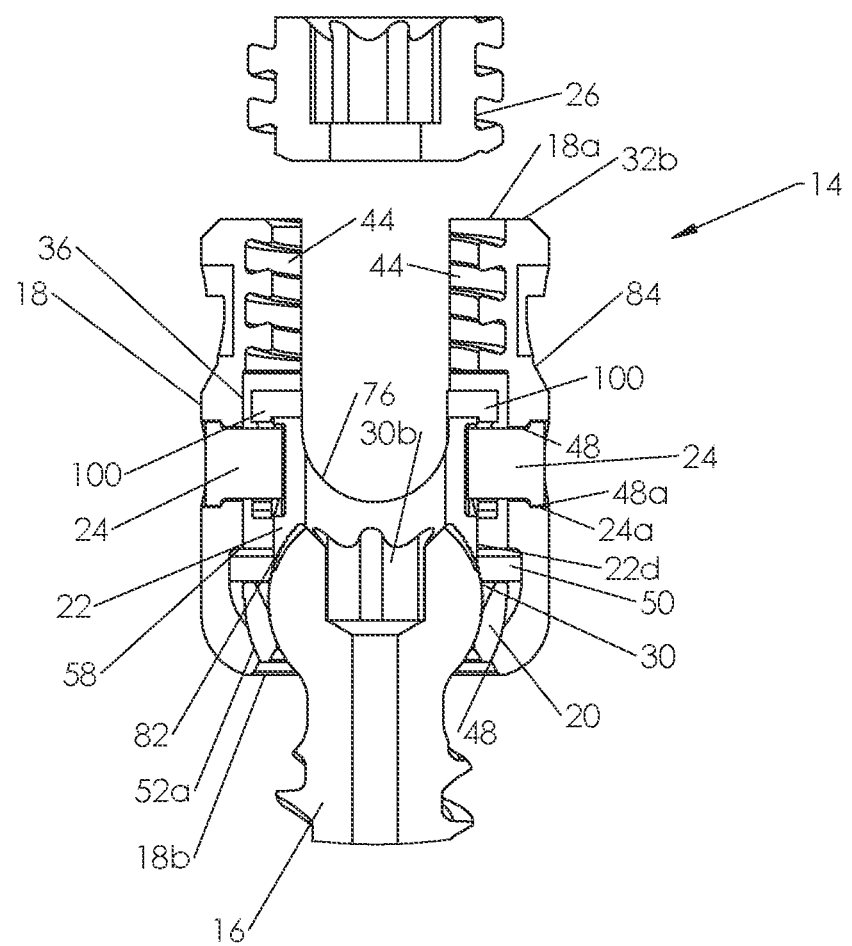

FIG. 15 is a cross-sectional view of the modular yoke assembly in a state of being assembled to the pedicle screw.

Figure 16:
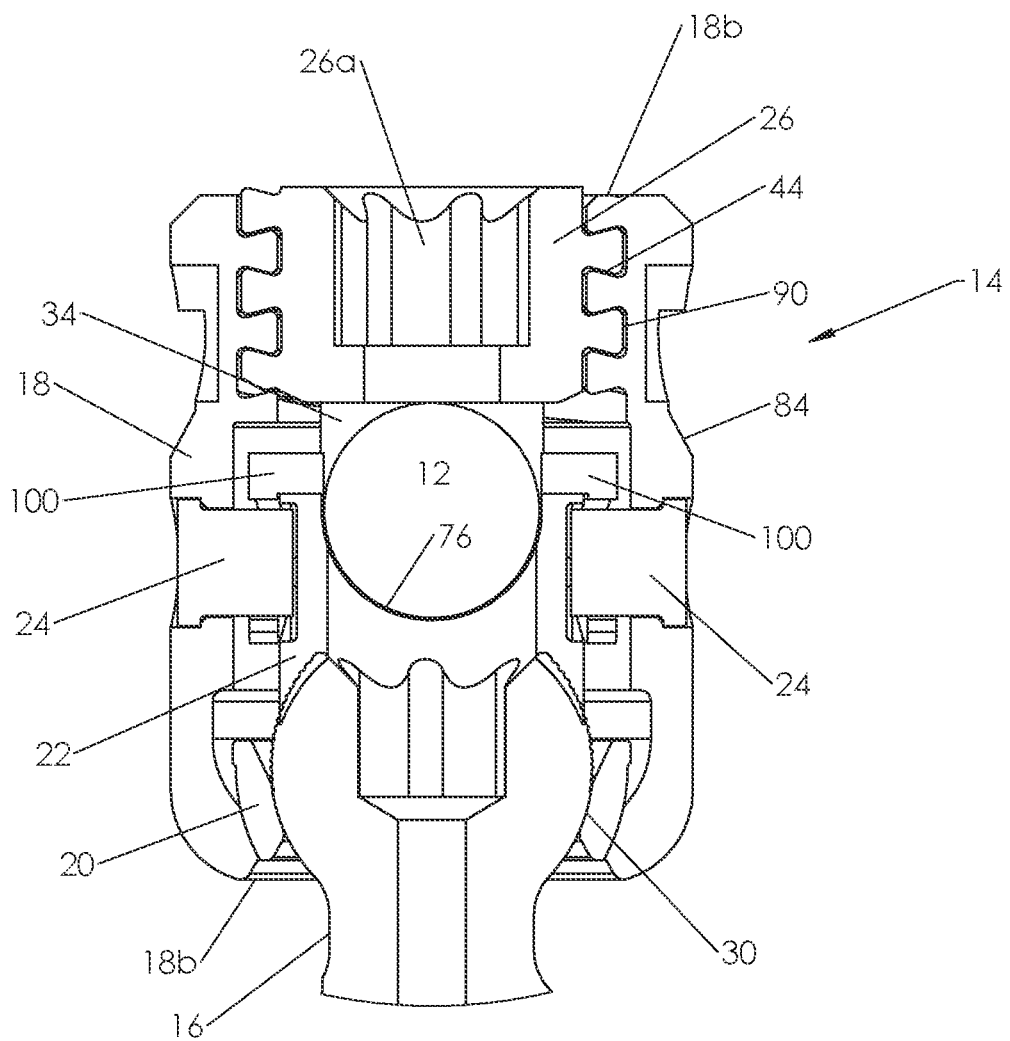

FIG. 16 is a cross-sectional view of the modular tensioned polyaxial pedicle screw attached to a spinal rod.

FIG. 17 which includes FIGS. 17A through 17C illustrates a second embodiment of a tension member, with FIG. 17A showing a side elevation view of the tension member, FIG. 17B showing a front perspective view of the tension member, and FIG. 17C showing a rear perspective view of the tension member.

FIG. 18 which includes FIGS. 18A through 18C illustrates a third embodiment of a tension member, with FIG. 18A showing a side elevation view of the tension member, FIG. 18B showing a front perspective view of the tension member, and FIG. 17C showing a rear perspective view of the tension member.

Figure 19A:
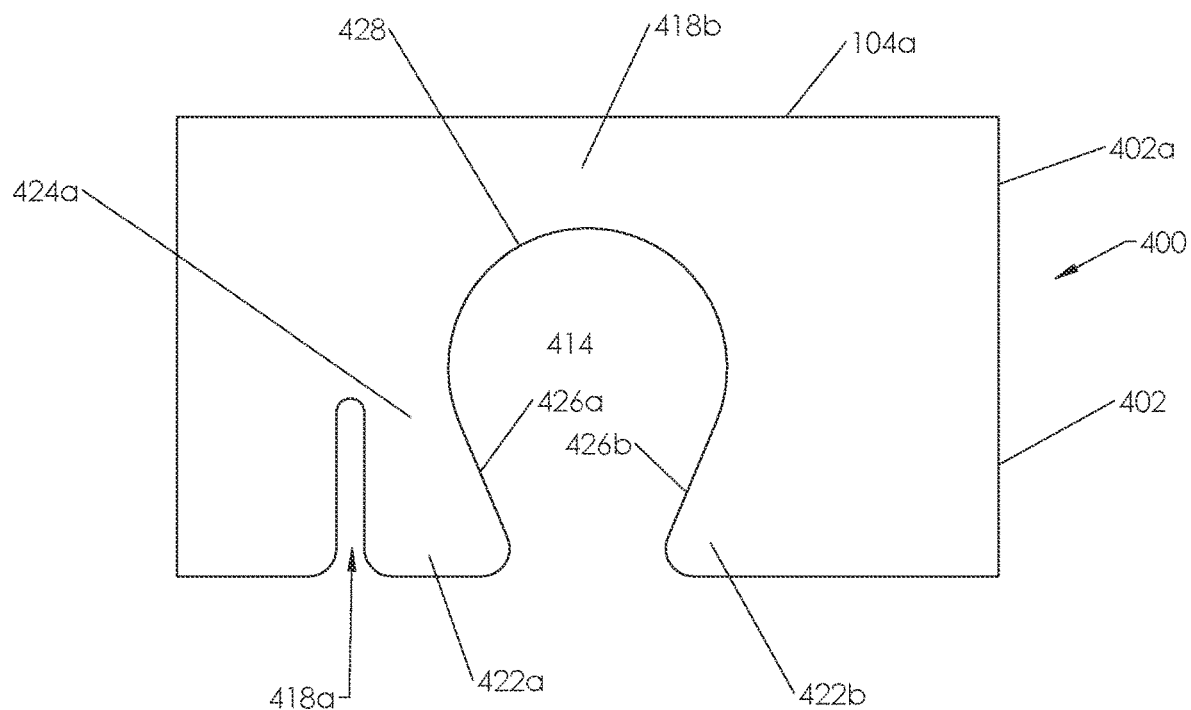
Figures 19, 19B, 19C:
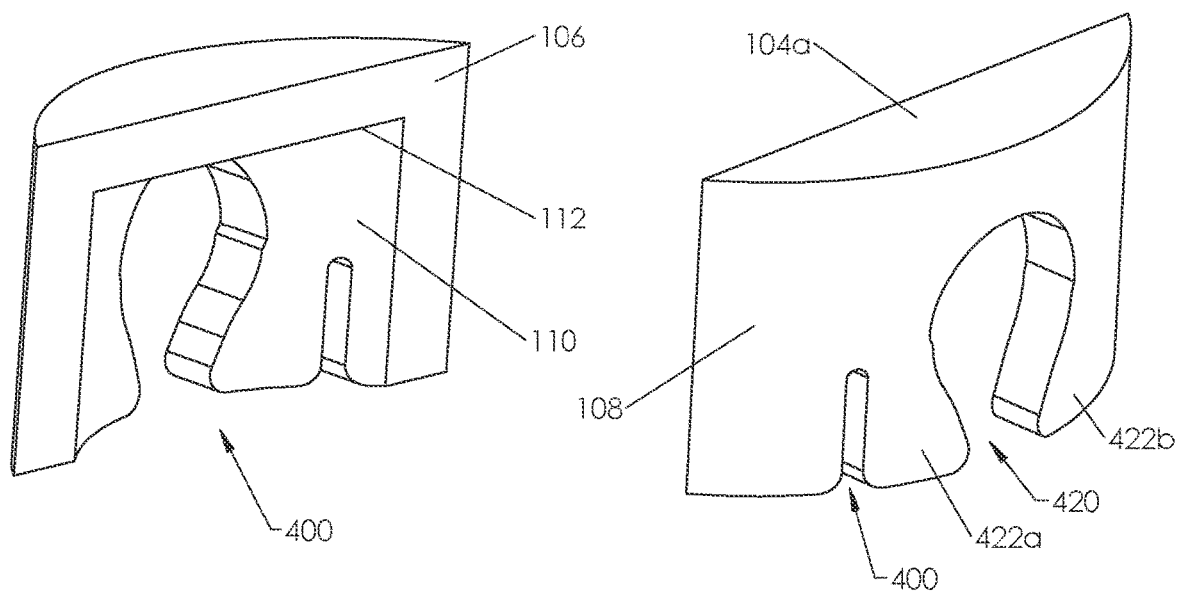

FIG. 19 which includes FIGS. 19A through 19C illustrates a fourth embodiment of a tension member, with FIG. 19A showing a side elevation view of the tension member, FIG. 19B showing a front perspective view of the tension member, and FIG. 19C showing a rear perspective view of the tension member.

Figure 20A:
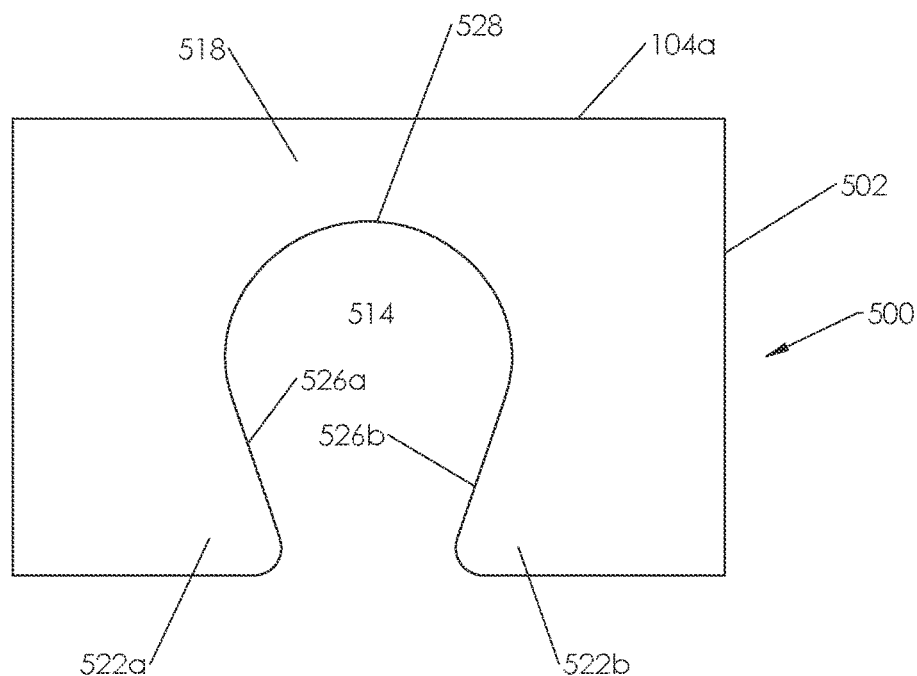
Figures 20, 20B, 20C:
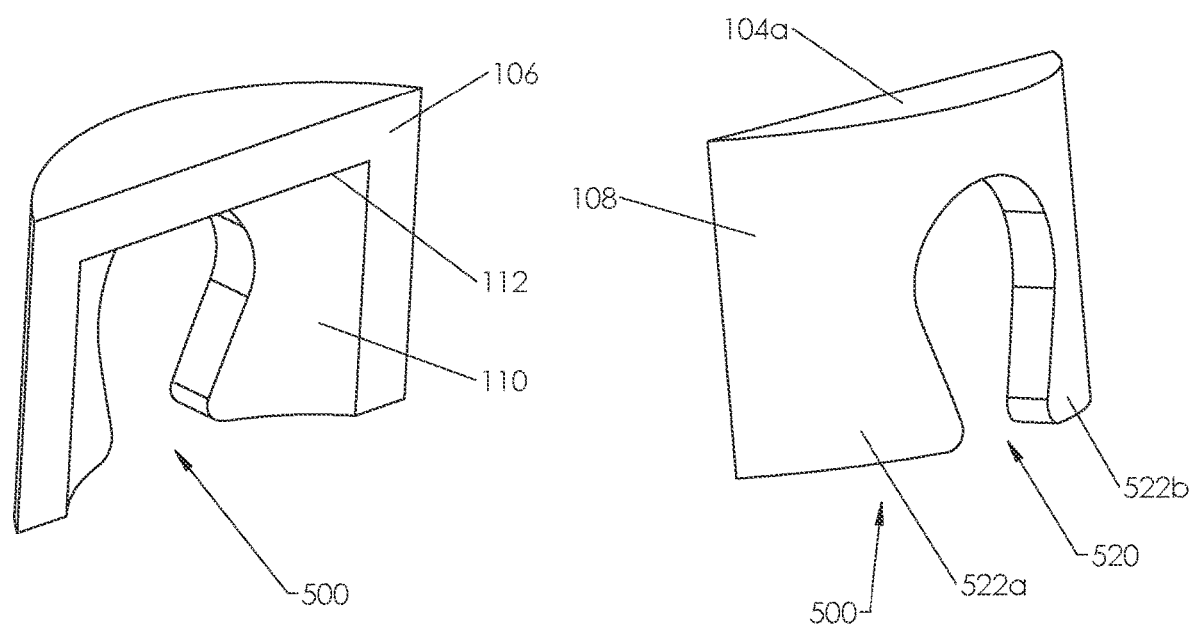

FIG. 20 which includes FIGS. 20A through 20C illustrates a fifth embodiment of a tension member, with FIG. 20A showing a side elevation view of the tension member, FIG.

20B showing a front perspective view of the tension member, and FIG. 20C showing a rear perspective view of the tension member.

FIG. 21 which includes FIGS. 21A through 21C illustrates a sixth embodiment of a tension member, with FIG. 21A showing a side elevation view of the tension member, FIG. 21B showing a front perspective view of the tension member, and FIG. 21C showing a rear perspective view of the tension member.

Figure 22:
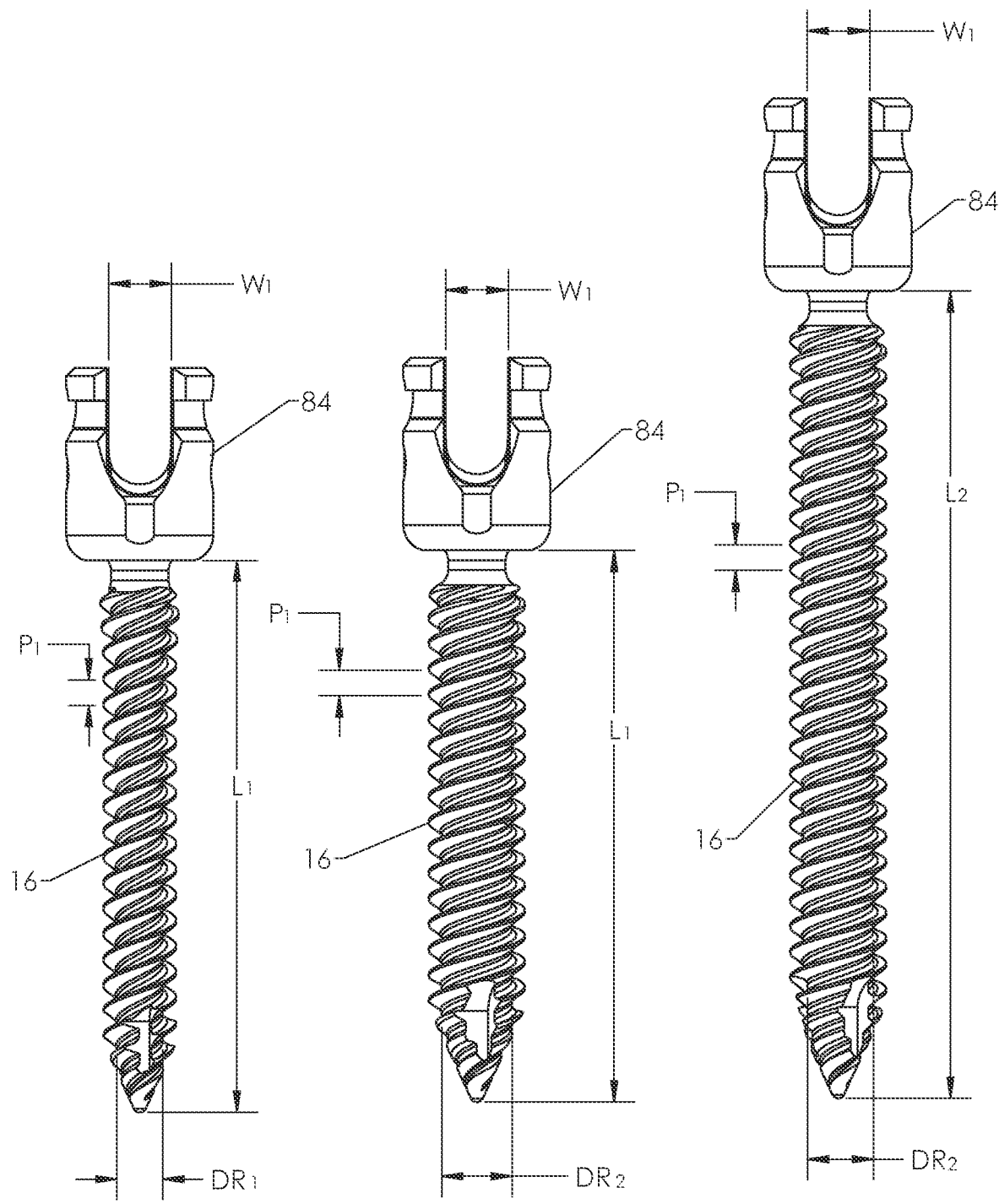
Figure 23:
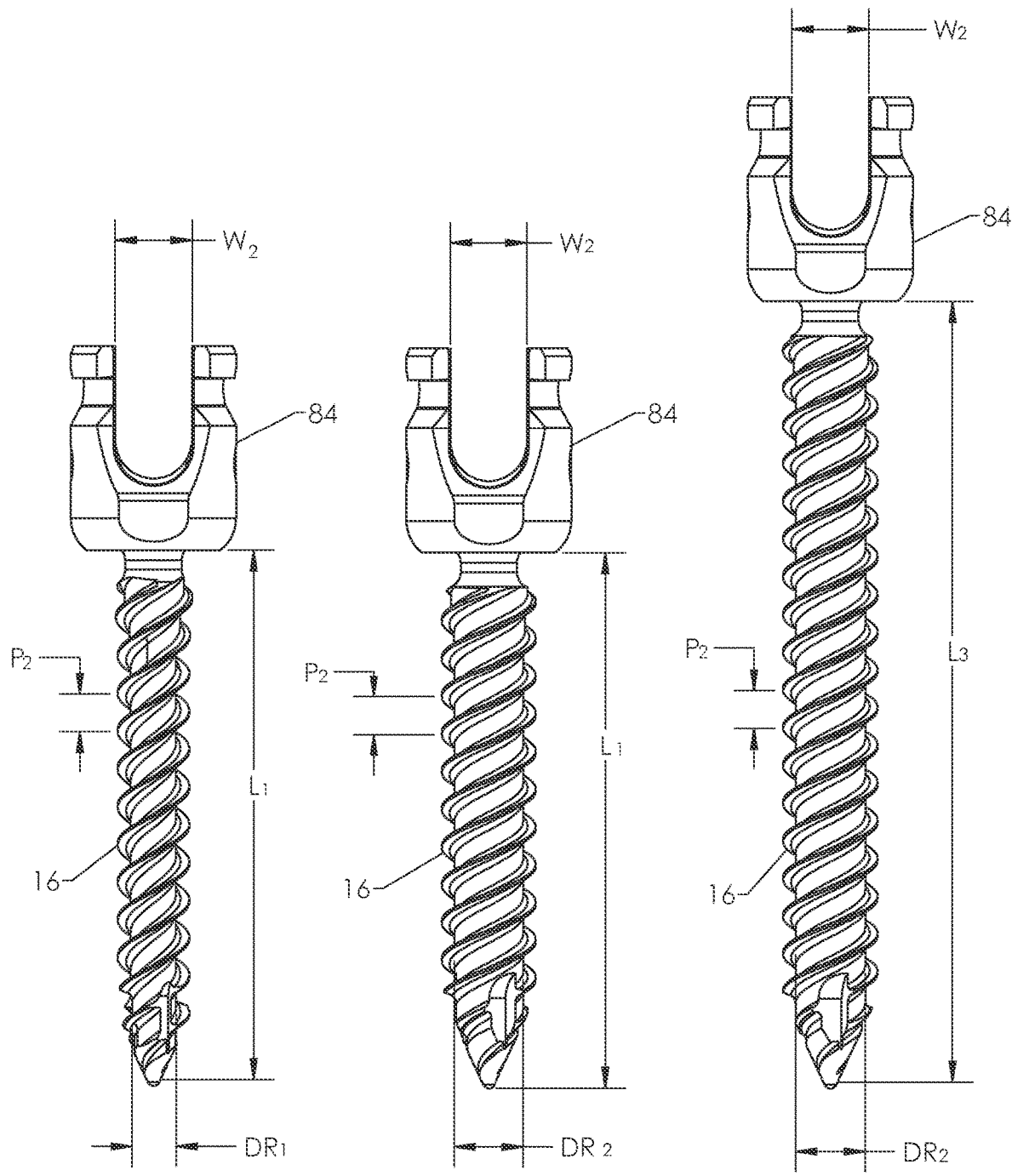

FIGS. 22 and 23 illustrate kits of parts for use in spinal surgery that comprise a plurality of differently dimensioned bone screws and yoke assemblies.

DETAILED DESCRIPTION OF THE EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
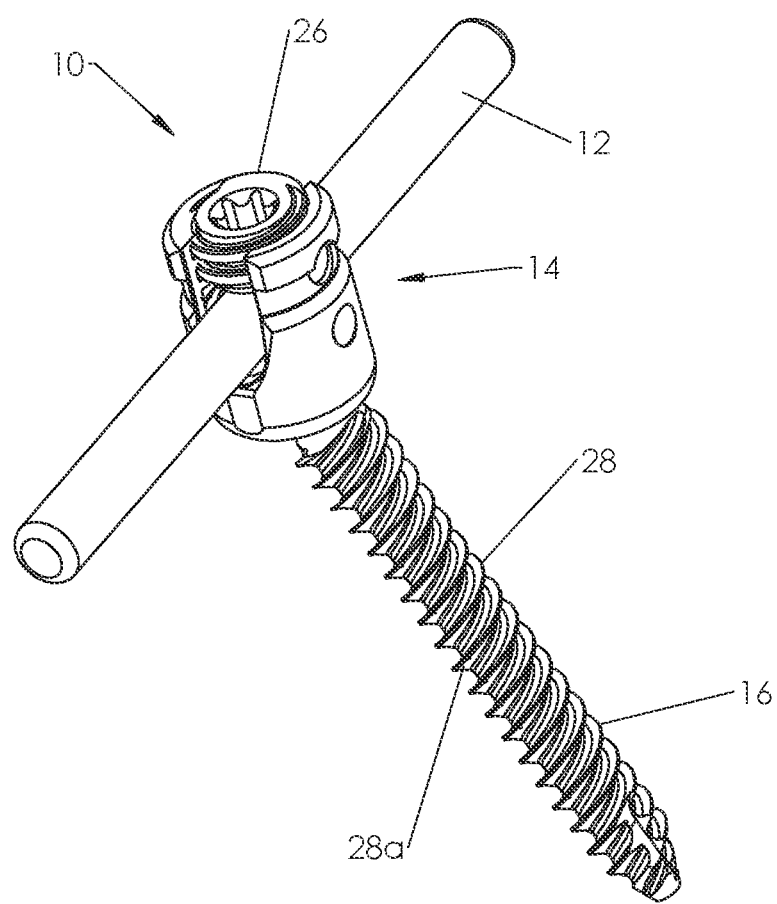
FIG. 1 is a top perspective view of a spinal fixation system utilizing a modular tensioned polyaxial pedicle screw in accordance with an embodiment of the present invention, shown in connection with an elongate connecting rod.

The present invention has particular facility in a spinal fixation system, such as the system 10 depicted in FIG. 1. As is known in the art, such a spinal fixation system 10 spans between successive vertebrae of the spine. An elongated member, such as a connecting rod 12, extends along a length of the spine and provides an anchor point for connecting each vertebra to the system 10. The rod 12, typically formed of stainless steel, is contoured by bending to approximate the normal curvature of the spine for the particular instrumented spinal segments. An anchor device is provided for connecting each of the vertebral segments to the rod 12. These anchor devices may include hooks, bolts, screws or other means for engaging a vertebra. For the purposes of the present invention, the spinal anchor device is a polyaxial bone screw 14. More specifically, polyaxial bone screw 14 is a modular tensioned polyaxial pedicle screw. In a particular example, modular tensioned pedicle screw 14 is configured and sized for connection to the thoraco-lumbar region of the spine from the posterior direction for threaded engagement with a pedicle of a vertebra. Configurations for use in other regions of the spine and from other directions are also contemplated.

Referring now to FIG. 2, the elements of modular tensioned polyaxial pedicle screw 14 are shown in exploded view. Modular tensioned screw 14 comprises a threaded bone fastener 16, a yoke 18, an expandable socket collar 20, a saddle 22, a pair of connecting yoke pins 24, a fastening element 26 in the form of a locking screw, and in one arrangement, a pair of oppositely disposed tension members 100.

Fastener 16 in a particular arrangement is a bone screw, preferably a pedicle screw. Threaded shank 28 has threads 28a configured for threaded engagement within a portion of a vertebra, such as the pedicle. Bone screw 16 may, however, be introduced into the medial cortical aspect of the vertebra, particularly when used in the thoraco-lumbar region of the spine. Screw head 30 has an outer surface 30a, having in a particular arrangement, a spherical configuration. Screw head 30 includes an interior socket 30b formed to have a hex-shape or other suitable configuration for receipt of a driver instrument (not shown) for inserting screw 16 into the vertebra. In one arrangement, screw head 30 has exterior ridges or is treated with a suitable surface treatment such as grit blasting to render outer surface 30a abrasive to enhance rigid, locking engagement, as will be described.

Figure 3:
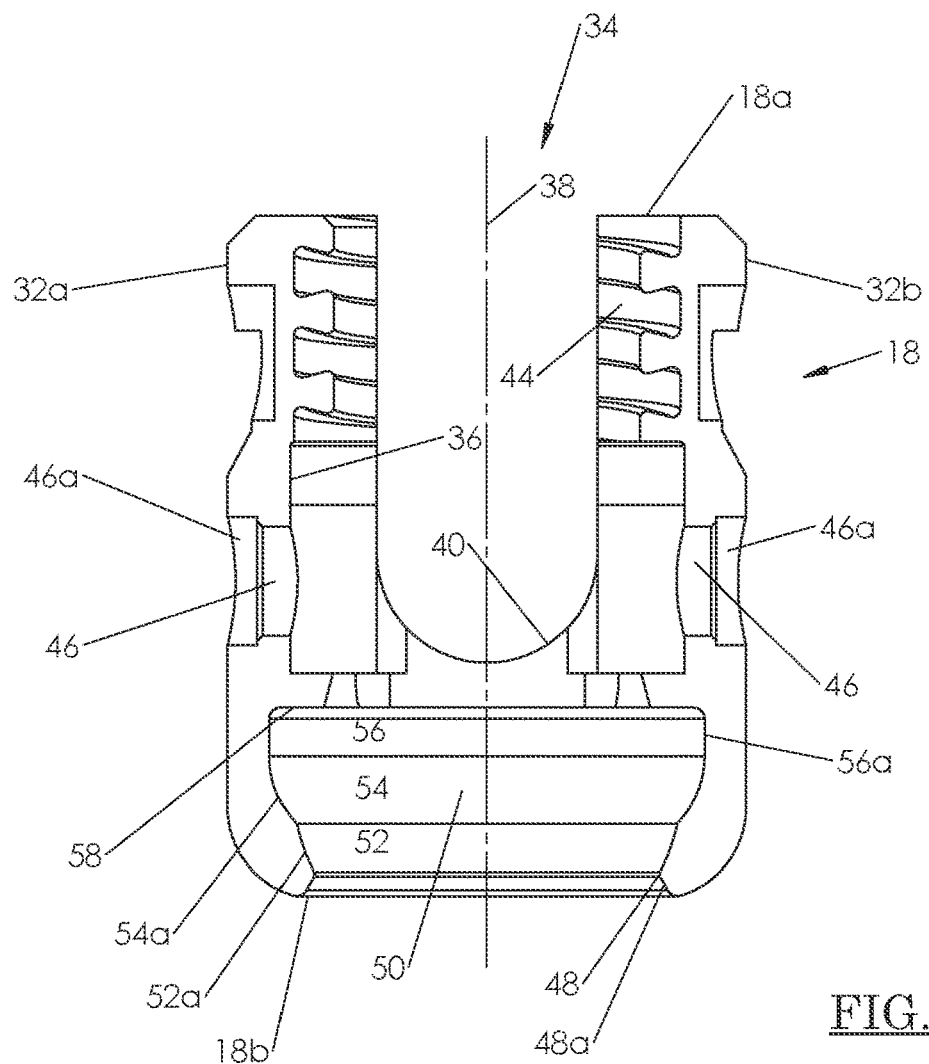
FIG. 3 is a cross-sectional view of the yoke of the modular tensioned polyaxial pedicle screw of FIG. 2
Figure 5:
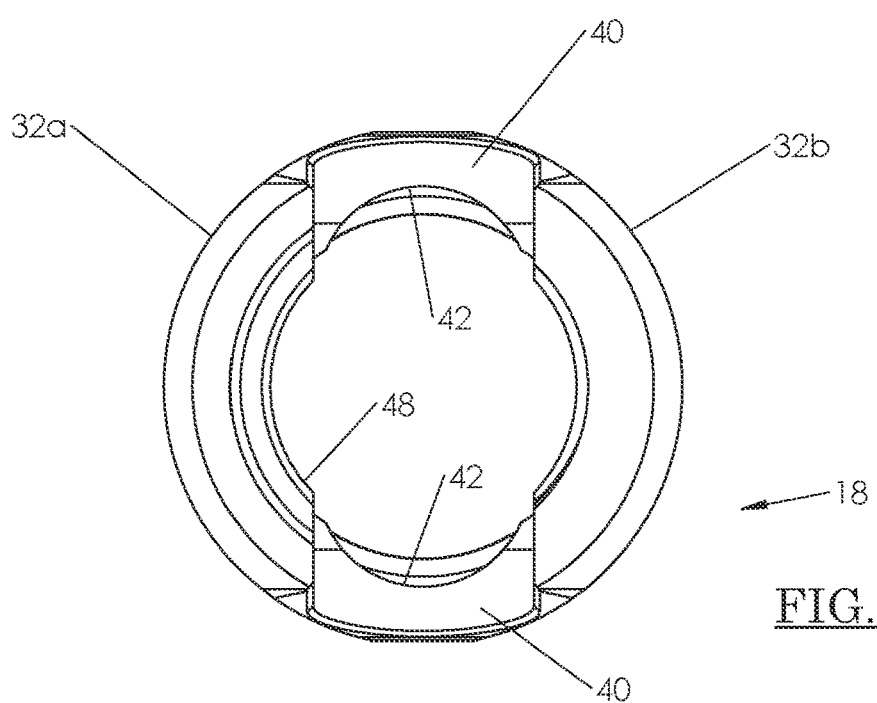
FIG. 5 is a top plan view of the yoke of FIG. 2.
Figure 4:
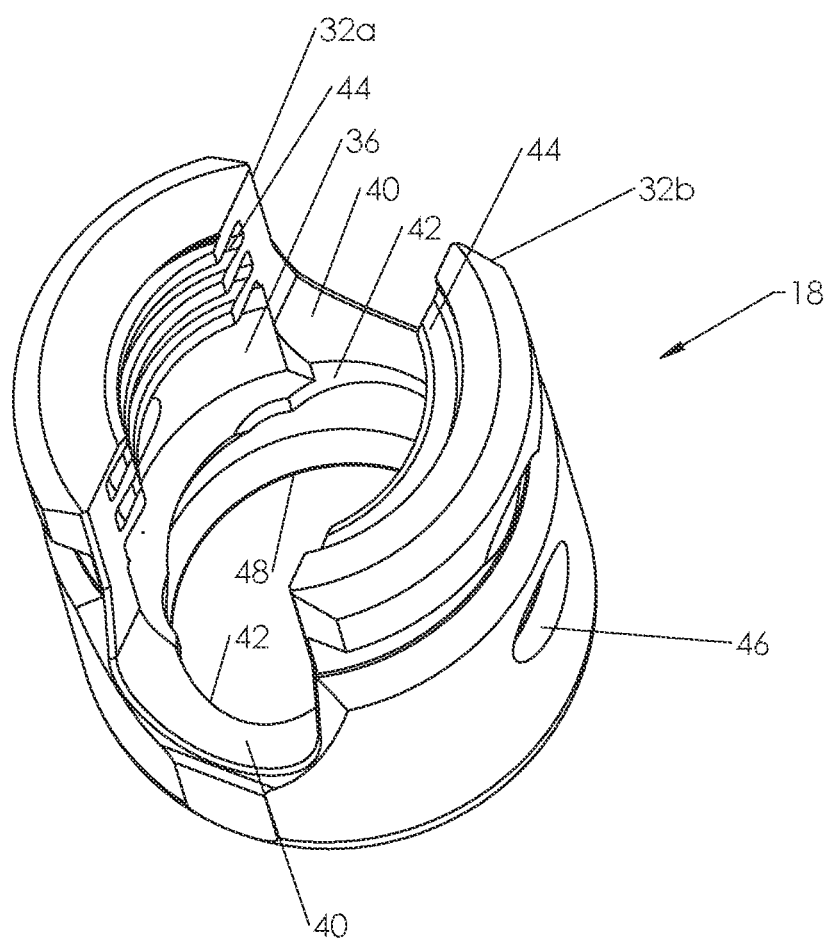
FIG. 4 is a top perspective view of the yoke of FIG. 2.

Turning now also to FIG. 3-5, details of yoke 18 are described. Yoke 18 is of generally cylindrical configuration having an upper end 18a and an opposite lower end 18b. Yoke 18 includes a pair of spaced opposing arms 32a and 32b that define therebetween a U-shaped yoke channel 34 that extends through yoke upper end 18a. The spacing between arms 32a and 32b defines the width of channel 34 and is sized to closely fit the outer diameter of spinal rod 12 (as best seen in FIG. 16). Yoke 18 has an inner central bore 36 defined by a bore diameter extending longitudinally therethrough that defines a yoke axis 38 extending longitudinally through upper end 18a and lower end 18b. Yoke 18 includes a pair of opposing surfaces 40 at the bottom of channel 34, surfaces 40 extending between and joining yoke arms 32a and 32b and communicating with central bore 36. The bottom surfaces 40 in one arrangement are formed as curved surfaces. Cutouts 42 are formed into each of bottom surfaces 40 in alignment and communication with channel 34 to receive a portion of saddle 22, as will be described. Arms 32a and 32b define internal threads 44 for engaging fastening element 26. In a particular arrangement, threads 44 are formed in a conventionally known bowtie configuration that cooperates with a similar bowtie external thread configuration on fastening element 26 to provide an anti-splaying construct. Holes 46 are formed through each of arms 32a and 32b transversely relative to yoke axis 38 in communication with channel 34 for receipt of connecting pins 24, as will be described. In one arrangement each pin 24 is formed as a cylindrical post (see FIG. 2) having a length along a longitudinal axis and an outer diameter to fit relatively closely through a respective hole 46, each hole 46 being formed to have a circular diameter. Each pin 24 may further include a head 24a with an enlarged diameter greater than the diameter of hole 46 to fit into a counterbore 46a communicating with each hole 46. The length of each pin 24 is configured such that upon insertion of pin 24 into a respective hole 46 and disposition of head 24a in a counterbore 46a, the distal end of each pin 24 extends into inner central bore 36 of yoke 18 (as illustrated in FIG. 10).

Referring further to FIG. 3, the opposite lower end 18b of yoke 18 is formed to have a lower opening 48 and a lower interior cavity 50, lower interior cavity 50 communicating with lower opening 48 and central bore 36. Lower opening 48 has a diameter greater that the maximum diameter of head 30 of bone screw 16 such that head 30 may be bottom loaded through lower opening 48. An outwardly downwardly flared chamfer 48a may be formed at the bottom of lower opening 48. Lower interior cavity 50 has a first region 52, a second region 54 and a third region 56. First region 52 communicates with lower opening 48 and preferably has a first partially spherical internal surface 52a having a first radius of curvature. First region 52 has a portion that is diametrically wider than the diameter of opening 48. Second region 54 communicates with first region 52 and preferably has a second partially spherical internal surface 54a having a second radius of curvature. The second radius of curvature of second internal surface 54a is in one arrangement less than the first radius of curvature of first internal surface 52a. Second region 54 has a portion that is diametrically wider than the widest diameter of region 52. Third region 56 communicates with second region 54 and preferably has a cylindrical internal surface 56a. Third region 56 is substantially as wide as the widest portion of second region 54 and greater than the diameter defining yoke bore 36. Third region 56 terminates interiorly of lower interior cavity 50 in an interior stop surface 58 that extends transversely relative to yoke axis 38 between surface 56a and yoke bore 36. Formation of the cylindrical region 56 allows for expansion of socket collar 20 and for lower end 18b of yoke 18 to have sufficient strength for subsequent attachment to the head 30 of bone screw 16, as will be described.

Figure 6:
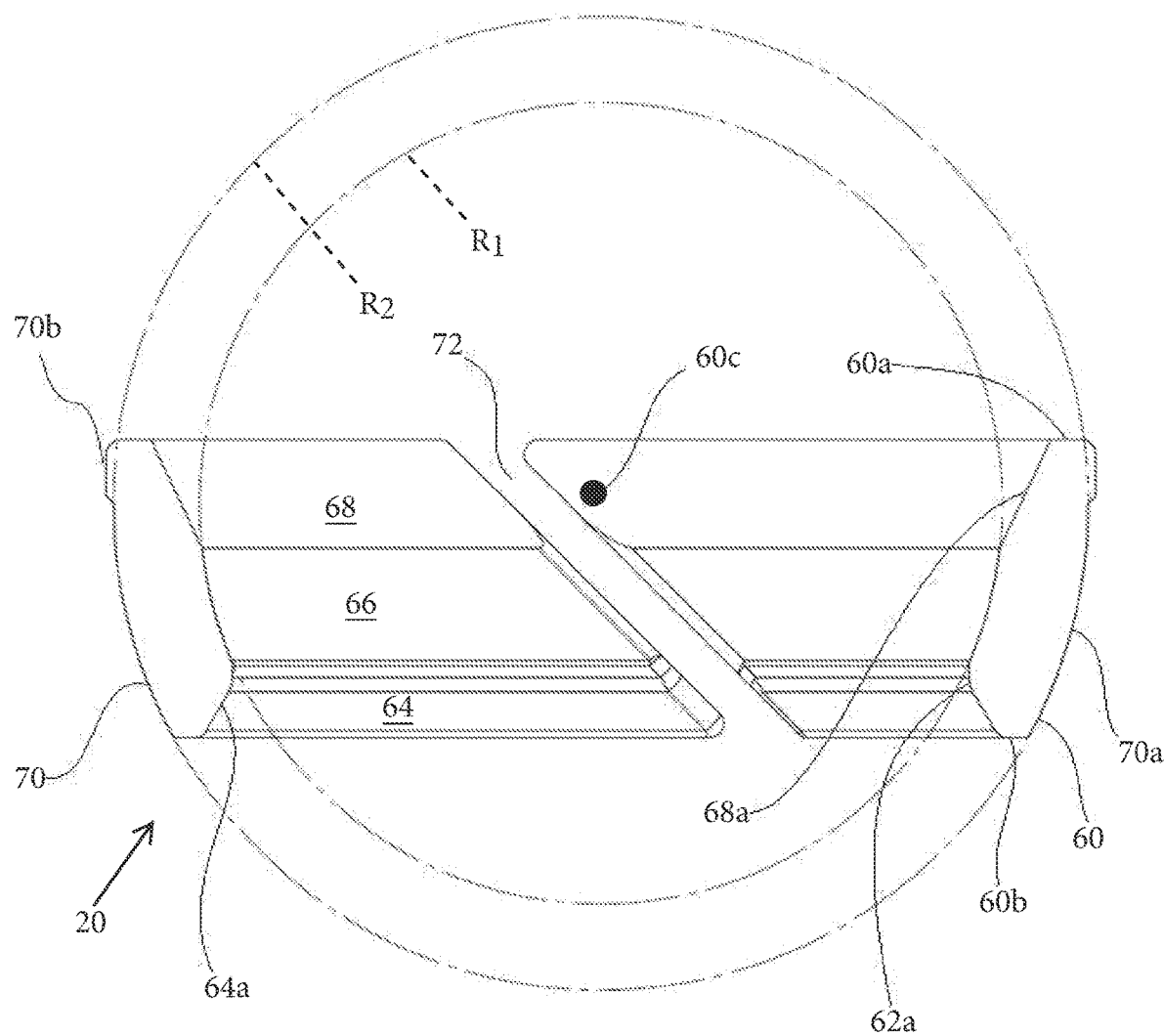
FIG. 6 is a side elevation view of the socket collar of the modular tensioned polyaxial pedicle screw of FIG. 2.

Referring now to FIG. 6, details of socket collar 20 are described. Collar 20 comprises a ring 60 of generally circular configuration having a generally circular central opening 62. Ring 60 includes a top surface 60a and a bottom surface 60b that in one arrangement are substantially parallel. Opening 62 has a first portion 64, a second portion 66 and a third portion 68. First portion 64 preferably has a first outwardly downwardly flared chamfer 64a formed into the bottom surface 60b of ring 60. Second portion 66 communicates with first portion 64 and preferably has a partially spherical internal surface 66a having a radius of curvature, $R_1$ that extends around a center point 60c. The radius of curvature of internal partially spherical surface 66a is in one arrangement substantially the same as the radius of curvature of the outer spherical surface 30a of bone screw head 30. Third portion 68 communicates with second portion 54 and preferably has a frusto-conical internal surface 68a extending to top surface 60a. Ring 60 has an outer surface 70 that preferably includes a partially spherical external surface 70a extending from bottom surface 60b of ring 60 toward the top surface 60a. Partially spherical external surface 70a has a radius of curvature, $R_2$ that is greater than the radius of curvature, $R_1$ of internal surface 66a and also extends around center point 60c. The radius of curvature of external partially spherical surface 70a is in one arrangement substantially the same as the radius of curvature of first partially spherical surface 52a in the lower interior cavity 50 at the lower end 18b of yoke 18. Adjacent top surface 60a of ring 60 outer surface 70 includes a generally cylindrical surface defining a ring rim 70b. In a preferred arrangement, ring 60 is split as defined by a gap 72 that extends angularly through ring 60. Gap 72 allows a certain amount of radial expansion and contraction of ring 60. The intersection of flared chamfer 64a and partially spherical surface 66a defines the narrowest dimension 62a of opening 62. In the unexpanded condition of socket collar 20, dimension 62a is less than the maximum diameter of head 30 of bone screw 16 such that head 30 may not pass therethrough unless socket collar 20 is expanded.

Figure 7:
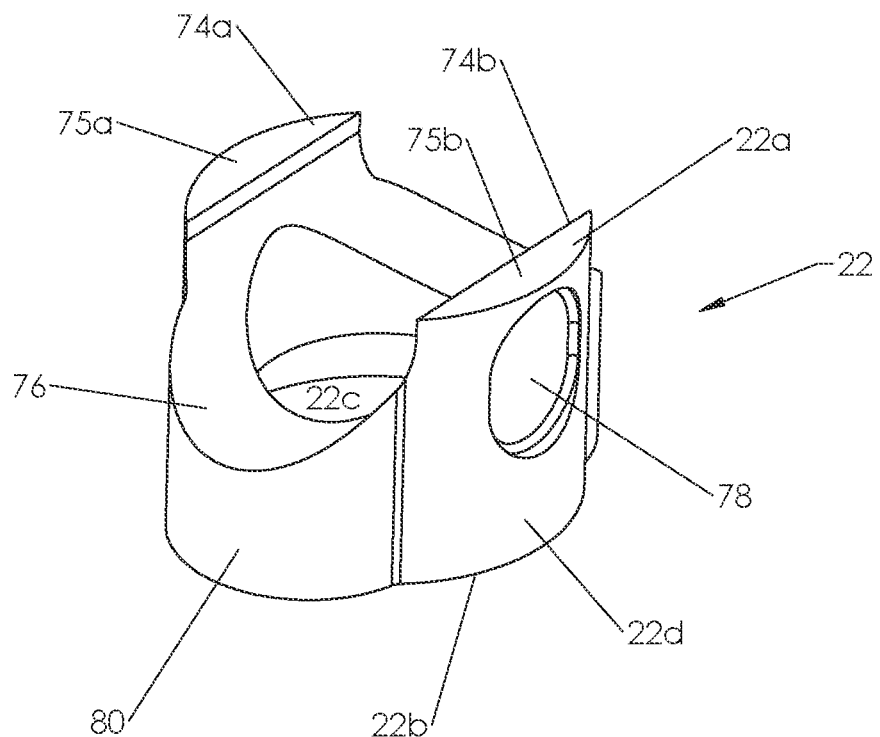
FIG. 7 is a top perspective view of the saddle of FIG. 2.
Figure 8:
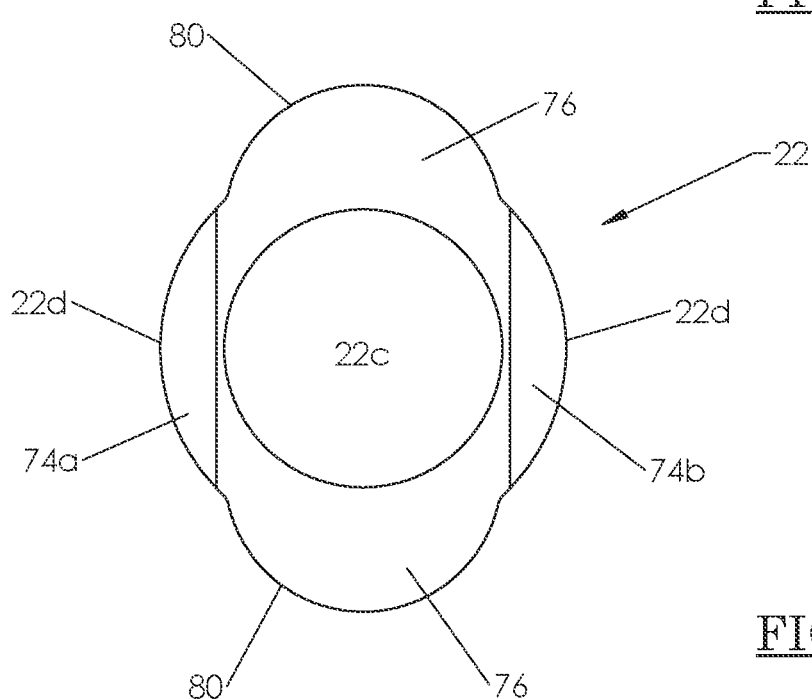
FIG. 8 is a top plan view of the saddle of FIG. 2.

Referring now to FIGS. 7-8, further the details of the saddle 22 are described. Saddle 22 is of generally cylindrical configuration having an upper end 22a and an opposite lower end 22b with a bore 22c extending therethrough. Saddle 22 includes a pair of spaced opposing walls 74a and 74b that define therebetween a curved cradle 76 facing toward upper end 22a and extending on opposite sides of bore 22c. The upper ends of each wall 74a and 74b terminate respectively in a flat top surface 75a and 75b, which serve as contact surfaces for tension member 100, as will be described. Curved cradle 76 is sized and configured to receive spinal rod 12, as shown in FIG. 1. A pair of recesses 78 elongated in the axial direction are formed into but not through the exterior surfaces of walls 74a and 74b for receipt of connecting pins 24, as will be described. The axial length of elongated recesses is greater than the diameter of pins 24, thereby allowing a limited degree of axial movement of saddle 22 relative to pins 24 once assembled, as will be described. As best seen in FIG. 8, saddle 22 includes a pair of lobes 80 that project outwardly from saddle 22 in alignment and preferably merging with curved cradle 76. Exteriorly between lobes 80 saddle 22 includes a generally cylindrical body 22d having a diameter slightly smaller than the diameter defining yoke bore 36. A The lower surface 82 at the lower end 22b of saddle 22 (see FIG. 10) is formed to have a partially spherical concave surface having a radius of curvature that in one arrangement is substantially the same as the radius of curvature of the outer spherical surface 30a of bone screw head 30.

Turning now to FIGS. 9 and 9A through 9D, details of tension member 100 in accordance with a first embodiment are described. Tension member 100 comprises a body 102 having an upper end 102a and an opposite lower end 102b. Upper end 102 terminates in substantially flat surface 104a and lower end 102b terminates a substantially flat bottom surface 104b. Extending between top surface 104a and bottom surface 104b is a first outer surface 106 and a second surface 108. In one arrangement, first outer surface 106 is substantially flat and second outer surface 108 is curved with its edges intersecting inner surface 106 as illustrated in FIGS. 9B and 9C. As such, tension member body 102 has a generally truncated semicircular configuration. The radius of curvature of second outer surface 108 is closely configured to the radius of curvature of inner central bore 36 of yoke 18 such that in assembly, as will be described, outer surface 108 lies closely adjacent inner surface of inner central bore 36.

A pocket 110 is formed to extend into first outer surface 106, pocket 110 being defined in part by a pressure surface 112 extending transversely relative to first outer surface 106, as shown in FIGS. 9C and 9D. In communication with pocket 110, tension member body 102 has a retention member opening 114 extending therethough opening 114 terminating in a narrower throat 116 at the bottom surface 104b of tension member body 102. Opening 114 has a dimension greater than the outer diameter of cylindrical pin 24 for receipt therein of cylindrical pin 24, as will be described. The maximum expanded dimension of throat 116, however, is less than the diameter of cylindrical pin 24 so that pin 24 may not slide therethrough. Formed through tension member body 102 on each side of opening 114 is a slot 118a and 118b, each of which opens at bottom surface 104b and extends a distance toward upper end 102a of tension member body 102. In this first embodiment of tension member 100, slots 118a and 118b taper to a narrower width as each slot 118a and 118b extends toward upper end 102a of tension member body 102, as seen in FIG. 9A. Opening 114 and slots 118a and 118b together define a resilient biasing member 120 comprising a pair of resiliently deflectable spaced spring fingers 122a and 122b. Each of spring fingers 122aa and 122b is attached to tension member body 102 by an elastically flexible hinge 124a and 124b, extending respectively between slots 118a, 118b and opening 114 adjacent upper end 102 of tension member body 102. Interiorly of opening 114, each spring finger 122a and 122b includes a respective pin contact surface 126a and 126b for contacting cylindrical pin 24 to produce a biasing force, as will be described. Pin contact surfaces 126a and 126b may be curved in this arrangement. Tension member 100 may be formed of PEEK or titanium or any other suitable biocompatible material.

Having described details of the components of modular tensioned polyaxial pedicle screw 14, the assembly of the components to form a modular yoke assembly 84 prior to attachment to bone screw 16 is now described with reference to FIGS. 10-12. Yoke assembly 84 comprises yoke 18, socket collar 20, saddle 22, a pair of tension members 100 and a pair of cylindrical pins 24. Socket collar 20, saddle 22 and tension members 100 are sequentially introduced into yoke 18 in a top-loading process. Socket collar 20, introduced initially, is rotated 90° so that top surface 60a and bottom surface 60b of socket collar 20 respectively face threads 44 on the interior surfaces of opposing yoke arms 32a and 32b. In this manner socket collar 20, with slight contraction if necessary, is capable of passing through yoke bore 36 with the radial extremities of collar 22 extending through cutouts 42 until socket collar 20 reaches the wider lower interior cavity 50 at the lower end 18b of yoke 18. Socket collar 20 is then rotated 90° within lower interior cavity 50 back to the position shown in FIG. 10 wherein socket collar 20 rests floatingly on first partially spherical internal surface 52a of lower interior cavity region 52. Saddle 22 is then introduced into inner central bore 36 in a top-loading process whereby lobes 80 are oriented in alignment with yoke cutouts 42, as shown in FIG. 12. In this orientation, curved cradle 76 is in alignment with yoke channel 34.

Tension members 100 are then introduced, one at a time with a suitable tool exteriorly of saddle 22 and approximately diametrically apart. Each tension member 100 is positioned such that opposite portions of saddle cylindrical body 22d are received in a respective pocket 112 of a tension member 100. In such position, top surfaces 75a, 75b of each saddle 22 are in juxtaposition with a pressure surface 112 of a respective tension member 100, and an outer surface 108 of each tension member 100 is in close juxtaposition with inner central bore 36. of yoke 18, as illustrated in FIGS. 10 and 11. With a suitable tool holding saddle 22 and tension members 100 in position pins 24 are inserted into and through holes 46 in yoke walls 18a and 18b, through retention member openings 114 of respective tension members 100, and into respective recesses 78 of saddle 22 until the enlarged heads 24a of pins 24 bottom out in respective counterbores 46a. Pins 24 are then fixedly secured to yoke 18, such by laser welding, thereby captively retaining saddle 22 and tension members 100 in yoke 18 and substantially preventing rotation of saddle 22 relative yoke 18. Due to the elongation of recesses 78 along the axial direction, which elongation is greater than the diameter of respective pins 24 as noted above, saddle 22 is capable of a small limited amount of axial movement within yoke bore 36 prior to bone screw 16 being locked in position relative to yoke 18, as will be described. Yoke assembly 84 as so formed is thereby ready for use in attachment to a bone screw 16 which may be selected from a variety of different sizes during a surgical procedure. While two tension members 100 have been disclosed herein in the particular arrangement of yoke assembly 84, it should be appreciated that a tension member may be configured in manner as described herein such that a single tension member, or more than two may be included in a desired yoke assembly 84. While pins 24 have been described herein as retention members for supporting saddle 22 and tension members 22, as well as for providing a transverse surface against which biasing element 120 of tension member 100 is actuated it should be understood that these functions may also be achieved by a crimp or other surface extending into yoke inner bore 26.

In use for spinal surgery, a kit may be provided comprising a plurality of bone screws 16 and one or more yoke assemblies 84 as described hereinabove. The bone screws 16 in the kit may have different lengths (e.g., $L_1$, $L_2$, $L_3$), root diameters (e.g., $DR_1$, $DR_2$) and/or thread pitches (e.g., $P_1$, $P_2$) as shown in FIGS. 22 and 23. However, the heads 30 of each screw 16 are commonly formed to have a spherical surface having the same size and configuration such that any selected screw 16 may be attached to a selected yoke assembly 84. Each of yoke channels 34 may be configured to have a different width (e.g., $W_1$, $W_2$) dimension for receipt respectively of a spinal rod 12 having a different diameter. The lower opening 48 of each yoke 18 is configured, however, to have the same dimension for receipt therein of screws 16 having different lengths, root diameters and/or thread pitches, but having the same size head 30. In operation, a selected bone screw 16 is threaded into a vertebra 86, such as at a pedicle 88, as shown in FIG. 13. A suitable yoke assembly 84 is chosen for modular attachment in situ to the head 30 of inserted bone screw 16. Prior to attachment, the condition of tension members 100 in yoke assembly 84 is shown in FIG. 14A. In this position before use, a cylindrical pin 24 freely extends through retention member opening 114 of each tension member. With opening 114 having a greater dimension than the diameter of pin 24, an upper inner surface 128 of opening 114 contacts pin 24 and supports tension member 100 thereon. In this rest position, virtually no contact is made between pin 24 and pin contact surfaces 126a and 126b. As such there is no tension applied by spring fingers 122a and 122b. In addition, saddle 22 is independently movable to a limited degree relative to each tension member 100, with there being a slight space in this stage between each top surface 75a and 75b of saddle 22 and pressure surface 112 of a respective tension member 100.

The selected yoke assembly 84 is then mounted to an insertion tool for in situ attachment to the head 30 of bone screw 16. Insertion tool may be a tool such as that disclosed in commonly assigned Provisional Patent Application No. 62/853,831, entitled "Modular Spinal Screw Yoke Inserter", filed by Eugene Avidano, et al. on May 29, 2019, and in commonly assigned U.S. patent application Ser. No. 16/882,855, entitled "Modular Spinal Screw Yoke Inserter", filed by Eugene Avidano, et al. on May 26, 2020, and published as U.S. Patent Publication No. 2020/0375638, on Dec. 3, 2020, the entire contents of which are incorporated herein by reference. Once suitably mounted to the inserter, yoke assembly 84 may be pushed by the inserter on to head 30 of bone screw 16 to form the assembled modular tensioned polyaxial pedicle screw 14 as shown in FIG. 15. Upon downward movement of yoke assembly 84 onto head 30, head 30 moves socket collar 20 axially upwardly into the wider regions 54 and 56 of lower interior cavity 50 since head 30 cannot pass through collar opening 62 in the relaxed unexpanded condition. Upon further relative movement of head 30 upward and yoke assembly 84 downward, collar rim 70b will ultimately contact interior stop surface 58 within lower interior cavity 50. Continued movement of yoke assembly 84 downward will then push head 30 into collar opening 62 to expand the socket collar 20 radially via the split 72. During this movement bone screw head 30 will engage lower surface 82 of saddle 22 forcing saddle 22 upwardly until top surfaces 75a and 75b contact pressure surface 112 of each tension member. Upward movement of saddle 22 thereafter moves each tension member 100 upwardly relative to a respective pin 24. This upward movement of each tension member 100 causes contact between pin 24 and pin contact surfaces 126a and 126b. of spring fingers 122a and 122b as shown in FIG. 14B.

Once the spherical head 30 of bone screw 16 passes through collar opening 62 an audible click may be heard together with a tactile feel as socket collar 20 returns to its non-stressed radius. Further upward movement of bone screw 16 causes saddle 22 and tension members 100 to move jointly upwardly relative to respective pins 24 resulting in resilient flexing of spring fingers 122a and 122b about elastically flexible hinges 124a and 124b, as shown in FIG. 14C. The flexing of spring fingers 122a and 122b collapses each slot 118a and 118b, expands throat 116 and produces a resilient downward biasing force, F against each spring finger 122a and 122b. The maximum expanded dimension of throat 116 is less than the diameter of said cylindrical pin 24. The respective biasing forces, F are transferred to pressure surfaces 112 of each tension member 100 such that forces, F are then exerted on top surfaces 75a and 75b of saddle 22, urging saddle 22 resiliently downwardly. At this point, socket collar 20 will be disposed below the maximum diameter of head 30, as shown in FIG. 10. The inserter may then be manipulated to urge yoke assembly 84 upward causing socket collar 20 to move downward between the lower surface of head 30 and first partially spherical internal surface 52a at the lower end 18b of yoke 18. As so positioned, expansion of collar 20 is prevented and bone screw 16 cannot be withdrawn through opening 62. In such assembled but unlocked configuration, head 30 of bone screw 16 is compressed between saddle 22 and collar 20 by sufficient friction applied by tension members 100 to hold yoke 18 and bone screw 16 in a provisional position prior to locking with a spinal connecting rod 12. Yoke 18, however, may be moved polyaxially and rotationally relative to bone screw 16 upon application of a suitable manual force to overcome the frictional force.

Rod 12 or other fixation device can then be inserted into the U-shaped yoke channel 34 onto cradle 76 of saddle 22 as shown in FIG. 16. Locking screw 26 may then be threaded into threads 44 at upper 18a of yoke 18. Locking screw 26 may in one arrangement be formed to have external threads 90 in a bowtie configuration complementary with the bowtie internal threads 44 on yoke arms 18a and 18b. The bowtie configuration of the cooperative threads 44 and 90 assist to prevent or minimize splaying of arms 18a and 18b during threaded connection of locking screw 26. Locking screw 26 includes an interior socket 26a formed to have a hex-shape or other suitable configuration for receipt of a driver instrument (not shown) for threading locking screw 26 into the yoke threads 44. Upon tightening into yoke 18, locking screw 26 will engage rod 12 which is seated on curved cradle 76 of saddle 22. Continued tightening will push saddle 22 further downward along connecting pins 24 causing lower concave surface 82 of saddle 22 to forcibly engage head 30 of bone screw 16. This in turn moves head 30 further downward as yoke 18 moves relatively upward. Such relative movement causes the bottom of head 30 to forcibly engage socket collar 20 and wedge collar 20 rigidly against first partially spherical internal surface 52a at the lower end 18b of yoke 18, overcoming bias forces, F applied by tension members 100 and thereby locking head 30 between saddle 22 and socket collar 20. Upon complete tightening of locking screw 26, rod 12 and bone screw 16 are securely affixed to yoke 18 thereby preventing relative movement therebetween.

While the invention has been illustrated and described in detail in the drawings and foregoing description, the same should be considered as illustrative and not restrictive in character. For example, the configuration of tension member 100 as described herein is exemplary and may be formed in other suitable configurations to provide the desired tension in a modular tensioned spinal screw. FIGS. 17-21 illustrate five further exemplary embodiments of tension members that may be used in the context of the subject invention, it being understood that further variations may also be contemplated. These further exemplary embodiments include features that are common to the first embodiment of the tension member 100 described hereinabove and shown in FIGS. 9A-9D, and as such, those common features will have like reference numerals. It is also noted that each of the five further embodiments are formed to have a truncated semi-circular cross-section similar to that of tension member 100. In addition, each further embodiment has pocket 110 formed to extend into a first outer surface 106, pocket 110 being defined in part by a pressure surface 112 extending transversely relative to first outer surface 106. As described above, pressure surface 112 is configured to contact the top surface of saddle 22 so as to apply a downward force produced by tension member 100 onto saddle 22.

Turning now to FIGS. 17 and 17A through 17C, details of the tension member 200 in accordance with a second embodiment are described. In tension member 200, spring members 222a and 222b may have relatively linear pin contact surfaces 226a and 226b in communication with a retention member opening 214. Spring fingers 222a and 222b together define a resilient biasing element. 220. Opening 214 has a dimension greater than the outer diameter of cylindrical pin 24 for receipt therein of cylindrical pin 24, as described above. Slots 218a and 218b may each have a substantially uniform width over their respective lengths. Each of spring fingers 222a and 222b is attached to tension member body 202 by an elastically flexible hinge 124a and 124b, extending respectively between slots 218a, 218b and opening 214 adjacent upper end 202a of tension member body 202.

Turning now to FIGS. 18 and 18A through 18C, details of the tension member 300 in accordance with a third embodiment are described. In tension member 300, retention member opening 314 having a relatively rounded configuration. Opening 314 has a dimension greater than the outer diameter of cylindrical pin 24 for receipt therein of cylindrical pin 24, as described above. Spring fingers 322a and 322b are attached respectively to tension member body 302 by elastically flexible hinges 224a and 224b, extending respectively between slots 318a, 318b and opening 314 adjacent upper end 302a of tension member body 302. Spring fingers 322a and 322b together define a resilient biasing element. 320. Spring members 322a and 322b may have relatively linear pin contact surfaces 326a and 326b in communication with retention member opening 314. Slots 318a and 318b may have substantially uniform widths over there lengths with such lengths being shorter than the lengths of slots 218a and 218b of tension member 200. In addition, the thickness of tension member 300 between an upper inner surface 328 of opening 314 and top surface 104a of tension member 300 may be relatively thin to provide additional flexibility to spring members 322a and 322b.

Turning now to FIGS. 19 and 19A through 19C, details of the tension member 400 in accordance with a fourth embodiment are described. Tension member 400 is similar to tension member 300 except that only one slot 418a is provided, thereby defining first spring finger 422a attached to tension member body 402 by elastically flexible hinge 424a extending between slot 418a and opening 414. A second spring finger 422b is attached to tension member body 402 by an elastically flexible hinge 424b between an upper inner surface 428 of opening 414 and top surface 104a of tension member body 402 which is sufficiently thin to provide flexibility for spring member 422b. Spring fingers 422a and 422b together define a resilient biasing element. 420. Opening 414 has a dimension greater than the outer diameter of cylindrical pin 24 for receipt therein of cylindrical pin 24, as described above.

Turning now to FIGS. 20 and 20A through 20C, details of the tension member 500 in accordance with a fifth embodiment are described. Tension member 500 is similar to tension member 400 except that no slots are provided. Opening 514 has a dimension greater than the outer diameter of cylindrical pin 24 for receipt therein of cylindrical pin 24, as described above. Spring members 522a and 522b may have relatively linear pin contact surfaces 526a and 526b in communication with retention member opening 514. The thickness of tension member 500 between an upper inner surface 528 of opening 414 and top surface 104a of tension member 300 may be relatively thin to provide an elastically flexible hinge 518 about which spring members 522a and 522b may resiliently deflect. Spring fingers 522a and 522b together define a resilient biasing element. 520.

Turning now to FIGS. 21 and 21A through 21C, details of the tension member 600 in accordance with a sixth embodiment are described. Tension member 600 has a retention member opening 614 communicating with a flexible biasing member 620. Opening 614 has a dimension greater than the outer diameter of cylindrical pin 24 for receipt therein of cylindrical pin 24, as described above. Tension member 600 includes a pair of angularly disposed slots 618a and 618b that together with retention member opening 614 define a pair of elastically flexible hinges 624a and 624b. Flexible biasing member 620 includes a pin contact surface 626 in communication with retention member opening 614. Upon engagement with cylindrical pin 24 extending through retention member opening 614, flexible biasing member 620 may bend downwardly toward the bottom surface 104b about flex points 630a and 630b, causing contraction of slots 618a and 618b and further flexing about hinges 624a and 624b.

It should therefore be understood that only the preferred embodiments have been presented and that all changes, modifications and further applications that come within the spirit of the invention are desired to be protected.

What is claimed is:

1. A kit of parts for use in spinal surgery, comprising:
   a plurality of modular yoke assemblies, each modular yoke assembly comprising a monolithic one-piece, unitary yoke having an upper end, an opposite lower end and an inner central bore extending therethrough, said upper end including a pair of opposing arms spaced by a width and defining therebetween a channel for receipt of an elongate spinal rod, each of said channels being configured to have a different width for receipt respectively of a rod having a different diameter, said lower end of each yoke having a lower opening dimensioned for receipt therein of a head of a bone screw, the dimension of said lower opening of each yoke being the same, each yoke including within its inner central bore and at a location spaced from and not within said lower opening a tension member configured to apply upon receipt of said head of said bone screw a sufficient frictional force to hold said yoke in a provisional position that may be overcome by manual force; and
   a plurality of bone screws, each screw comprising a threaded elongate shaft having a length and a head at an upper end of said shaft, the length of each threaded elongate shaft being different, each said head having a spherical surface defining a diameter, the diameter of each head being the same.

2. The kit of parts of claim 1, wherein each of said bone screws has a different root diameter.

3. The kit of parts of claim 1, wherein each of said bone screws has a different thread pitch.

4. A kit of parts for use in spinal surgery, comprising:
   a plurality of modular yoke assemblies, each modular yoke assembly comprising a monolithic one-piece, unitary yoke having an upper end, an opposite lower end and an inner central bore extending therethrough, said upper end including a pair of opposing arms spaced by a width and defining therebetween a channel for receipt of an elongate spinal rod, said lower end of each yoke having a lower opening dimensioned for receipt therein of a head of a bone screw, the dimension of said lower opening of each yoke being the same, each yoke including within its inner central bore and at a location spaced from and not within said lower opening a tension member configured to apply upon receipt of said head of said bone screw a sufficient frictional force to hold said yoke in a provisional position that may be overcome by manual force; and
   a plurality of bone screws, each screw comprising a threaded elongate shaft having a length and a head at an upper end of said shaft, the length of each threaded elongate shaft being different, each said head having a spherical surface defining a diameter, the diameter of each head being the same.

5. The kit of parts of claim 4, wherein each of said channels is configured to have the same width.

6. The kit of parts of claim 4, wherein each of said bone screws has a different root diameter.

7. The kit of parts of claim 4, wherein each of said bone screws has a different thread pitch.

8. A kit of parts for use in spinal surgery, comprising:
   a plurality of modular yoke assemblies, each modular yoke assembly comprising a yoke having an upper end, an opposite lower end and an inner central bore extending therethrough, said upper end including a pair of opposing arms spaced by a width and defining therebetween a channel for receipt of an elongate spinal rod, each of said channels being configured to have a different width for receipt respectively of a rod having a different diameter, said lower end of each yoke having a lower opening dimensioned for receipt therein of a head of a bone screw, the dimension of said lower opening of each yoke being the same, each yoke including within its inner central bore and at a location spaced from and not within said lower opening a top-loaded tension member configured to be introduced through said upper end of said yoke into said central bore and to apply upon receipt of said head of said bone screw a sufficient frictional force to hold said yoke in a provisional position that may be overcome by manual force; and
   a plurality of bone screws, each screw comprising a threaded elongate shaft having a length and a head at an upper end of said shaft, each said head having a spherical surface defining a diameter, the diameter of each head being the same.

9. The kit of parts of claim 8, wherein the length of each threaded elongate shaft is the same.

10. The kit of parts of claim 8, wherein each of said bone screws has a different root diameter.

11. The kit of parts of claim 8, wherein each of said bone screws has a different thread pitch.

12. A kit of parts for use in spinal surgery, comprising:
   a plurality of modular yoke assemblies, each modular yoke assembly comprising a yoke having an upper end, an opposite lower end and an inner central bore extending therethrough, said upper end including a pair of opposing arms spaced by a width and defining therebetween a channel for receipt of an elongate spinal rod, each of said channels being configured to have the same width for receipt respectively of a rod having the same diameter, said lower end of each yoke having a lower opening dimensioned for receipt therein of a head of a bone screw, the dimension of said lower opening of each yoke being the same, each yoke including within said central bore a top-loaded saddle movably supported therein and a top-loaded tension member configured to apply upon receipt of said head of said bone screw in said lower opening and against said saddle a force to said saddle that provides sufficient friction to hold said yoke in a provisional position that may be overcome by manual force, each of said saddle and said tension member being configured to be introduced through said upper end of said yoke into said central bore; and a plurality of bone screws, each screw comprising a threaded elongate shaft having a length and a head at an upper end of said shaft, the length of each threaded elongate shaft being different, each said head having a spherical surface defining a diameter, the diameter of each head being the same.

13. The kit of parts of claim 12, wherein said saddle of each of said modular yoke assemblies is axially movable toward said upper end of said yoke upon receipt of the head of said bone screw into the lower opening of said yoke, said saddle having a top surface and an opposite lower surface, said lower surface being configured for contact with the head of said bone screw.

14. The kit of parts of claim 12, wherein a portion of said saddle of each of said modular yoke assemblies is received within a respective portion of each said tension member.

15. The kit of parts of claim 14, wherein each tension member has a pocket for receipt of said respective portions of each said saddle.

16. A kit of parts for use in spinal surgery, comprising:

a plurality of modular yoke assemblies, each modular yoke assembly comprising a yoke having an upper end, an opposite lower end and an inner central bore extending therethrough, said upper end including a pair of opposing arms spaced by a width and defining therebetween a channel for receipt of an elongate spinal rod, each of said channels being configured to have the same width for receipt respectively of a rod having the same diameter, said lower end of each yoke having a lower opening dimensioned for receipt therein of a head of a bone screw, the dimension of said lower opening of each yoke being the same, each yoke including within said central bore a saddle movably supported therein and a tension member configured to apply upon receipt of said head of said bone screw in said lower opening and against said saddle a force to said saddle that provides sufficient friction to hold said yoke in a provisional position that may be overcome by manual force; wherein said saddle of each of said modular yoke assemblies is axially movable toward said upper end of said yoke upon receipt of the head of said bone screw into the lower opening of said yoke, said saddle having a top surface and an opposite lower surface, said lower surface being configured for contact with the head of said bone screw, wherein each of said modular yoke assemblies further comprises a retention member extending within said inner central bore for supporting said saddle, and a plurality of bone screws, each screw comprising a threaded elongate shaft having a length and a head at an upper end of said shaft, the length of each threaded elongate shaft being different, each said head having a spherical surface defining a diameter, the diameter of each head being the same.

17. The kit of parts of claim 16, wherein said retention member of each of said modular yoke assemblies is a cylindrical pin having an outer diameter, and wherein the tension member includes a pin opening having a dimension greater than the outer diameter of said pin for receipt therethrough of a portion of said pin.

18. The kit of parts of claim 17, wherein said saddle of each of said modular yoke assemblies has an elongated recess formed in an exterior surface of said saddle in receipt of a portion of said pin.

* * * * *